(12) United States Patent
Wandinger-Ness et al.

(10) Patent No.: US 7,776,592 B2
(45) Date of Patent: Aug. 17, 2010

(54) HUMAN RENAL STEM CELLS

(75) Inventors: Angela Wandinger-Ness, Albuquerque, NM (US); Tamara Roitbak, Albuquerque, NM (US); Elsa G Romero, Rio Rancho, NM (US)

(73) Assignee: STC.UNM, Albuquerque, NM (US)

( * ) Notice: Subject to any disclaimer, the term of this patent is extended or adjusted under 35 U.S.C. 154(b) by 81 days.

(21) Appl. No.: 11/469,265

(22) Filed: Aug. 31, 2006

(65) Prior Publication Data

US 2007/0065942 A1    Mar. 22, 2007

Related U.S. Application Data

(60) Provisional application No. 60/713,081, filed on Aug. 31, 2005.

(51) Int. Cl.
 *C12N 5/071* (2010.01)
 *C12N 5/07* (2010.01)
 *A61K 48/00* (2006.01)

(52) U.S. Cl. .................. 435/369; 435/347; 435/366; 424/93.2

(58) Field of Classification Search .............. 435/369, 435/347, 366; 424/93.2
See application file for complete search history.

(56) References Cited

U.S. PATENT DOCUMENTS

| | | | |
|---|---|---|---|
| 6,410,320 B1 * | 6/2002 | Humes | 435/369 |
| 6,458,588 B1 | 10/2002 | Arnaout et al. | |
| 6,638,501 B1 * | 10/2003 | Bjornson et al. | 424/93.1 |
| 6,924,142 B2 | 8/2005 | Weiss | |
| 7,217,565 B2 * | 5/2007 | Buck et al. | 435/368 |
| 2002/0028510 A1 * | 3/2002 | Sanberg et al. | 435/368 |
| 2003/0082155 A1 | 5/2003 | Habener et al. | |
| 2003/0124093 A1 | 7/2003 | Rothanpieler et al. | |
| 2005/0169902 A1 | 8/2005 | Borlangan et al. | |
| 2006/0177925 A1 * | 8/2006 | Rosenberg et al. | 435/353 |

OTHER PUBLICATIONS

Bussolati et a. Am. J. Pathol. 166(2):545-555.*
Steenhard et al. J. Am. Soc. Neplhrol. 16:1623-1631; 2005.*
Oliver et al. J. Clin. Invest. 114: 795-804; 2004.*
Kleinman et al. J. Clin. Invest.80:1660-1669; 1987.*
Hong et al. Chin. Med. J. 116; 428-431; 2003.*
Oliver et al. J. Clin. Invest. 114: 795-804; Sep. 15, 2004.*

* cited by examiner

*Primary Examiner*—Fereydoun G Sajjadi
(74) *Attorney, Agent, or Firm*—Ellen M. Gonzales; Gonzales Patent Services

(57) ABSTRACT

The present disclosure provides human renal stem cells. Also described are human renal stem cells isolated from the papillary region of the human kidney and methods of isolating the same. Also described are methods for culturing, characterizing, and differentiating the same, including methods for identifying human renal stem cells that are positive for Nestin and CD133, and methods for allowing the cells to differentiate into neurons.

8 Claims, 7 Drawing Sheets

(7 of 7 Drawing Sheet(s) Filed in Color)

HUMAN RENAL STEM CELLS

CROSS-REFERENCE TO RELATED APPLICATION AND PRIORITY CLAIM

The present application claims priority to U.S. Provisional Patent Application Ser. No. 60/713,081 filed Aug. 31, 2005, the entirety of which is hereby incorporated by reference for all purposes.

BACKGROUND OF THE INVENTION

Many renal disorders, including acute and chronic kidney disease, common genetic diseases such as autosomal dominant polycystic kidney disease (ADPKD), renal cell carcinoma, glomerulonephritis and other pathological conditions, lead to kidney damage or loss. In the United States, approximately one person in five reaching 65 years of age will undergo organ-replacement during their remaining life span. It is predicted over 2 million patients will suffer from end-stage renal disease by 2010 [2]. Approximately 58,000 patients in the United States and 300 patients in New Mexico are currently on the waiting list for a kidney transplant, with some waiting for several years before an appropriate donor can be found. Substantial fractions of patients (12-17%) on the waiting list are designated as "most-difficult-to-transplant." Despite the advances in kidney transplantation, a significant shortage of donor organs severely limits treatment for these patients and requires many to remain on dialysis for extended periods of time. The quest for alternate organ restoration methods has resulted in rapid progression of new approaches, such as therapeutic cloning and embryonic/adult stem cell therapy (reviewed in 2-5).

The role of embryonic stem cells in the treatment of pathophysiological disorders has recently attracted significant interest and has been the subject of much controversy. The pluripotency of embryonic stem cells presents the possibility of their use for replacement of damaged kidney tissue. First indications show that mouse embryonic stem cells, develop an endoderm-like tissue in culture and in kidney transplants [6]. However, the in vitro generation of mesodermal precursors that give rise to the adult kidney remains unsubstantiated.

Furthermore, the transplantation of ES cells includes potential complications of immune rejection, teratomas and other cancers [4, 7]. The problems associated with the use of embryonic stem cells and the potential benefit of autologous transplantation has spurred an intensive search for adult stem cell populations. It is increasingly clear that stem cells may originate not only from embryonic, but also from adult tissue, including adult brain, bone marrow, skin and gut, where they can be recruited for organ repair after injury [8, 9]. Until recently, adult stem cells in kidney had not been identified [2-4, 10]. Progenitor-like cells involved in recovery from renal injury in an animal model were first identified in 2003 [11], and in 2004 a population of rodent adult kidney stem cells derived from rat and mouse renal papilla was isolated and characterized [1]. Adult rodent renal stem cells were identified on the basis of their low cell division rate. To detect them, a pulse of bromodeoxyuridine (BrdU) was administered to rat and mouse pups, and after 2-months, a small population of BrdU-positive cells was detected in the renal papilla. These cells had a plastic phenotype and, following injection into the renal cortex, they incorporated into the parenchyma. Adult renal stem cells exhibited features characteristic of other stem cells and expressed both mesenchymal and epithelial proteins [1]. However, while rats and mice serve as important animal models for human physiology, one cannot necessarily predict from the results obtained in a rat or mouse model system that the same results will be obtained in a human system. For example, differing results may be obtained between an animal model, such as rat and mouse, and the human system because of differences in the immune systems, physiology, life spans, and/or hematopoetic pathways between humans and rodents.

Another potential source for endogenous replacement of damaged or lost renal tubular epithelia may be surviving tubular epithelial cells themselves. These cells have a capacity to adapt to the loss of neighboring cells through dedifferentiation and proliferation. Both glomerular and tubular epithelial cells can regress to an embryonic mesenchymal phenotype and can either stimulate a regenerative potential of neighboring surviving cells or replace the damaged cells [10, 11]. A functional role of these cells in organ repair is based on their ability to migrate, proliferate and produce growth and trophic factors.

Accordingly, there remain many open questions regarding the characteristics that define adult human renal stem cells, as well as their precise differentiation potential. However, the identification of adult human renal stem cells holds promise for numerous benefits including the development of renal tissue replacement strategies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present disclosure provides a method for isolating adult human papillary cells that display stem cell markers and exhibit the capacity to differentiate toward different 20 lineages. The present disclosure further provides methods for determining if the renal papilla in humans provides a niche for a subpopulation of cells that serve as adult renal stem cells and that are able to differentiate into fully differentiated tubular epithelia.

Figure 1:
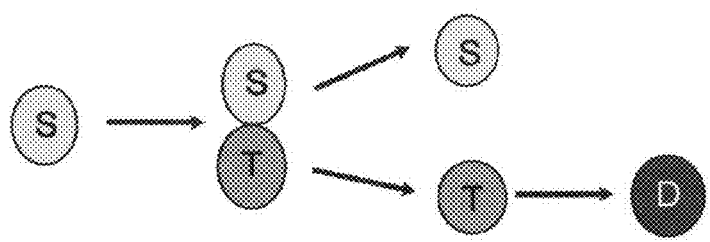
FIG. 1 is a schematic illustration of the asymmetric division of somatic stem cells. Asymmetric division of a stem cell (S) results in the generation of a stem cell and a transient amplifying precursor (T) that ultimately stops dividing and gives rise to a fully differentiated mature cell (D).
Figure 2:
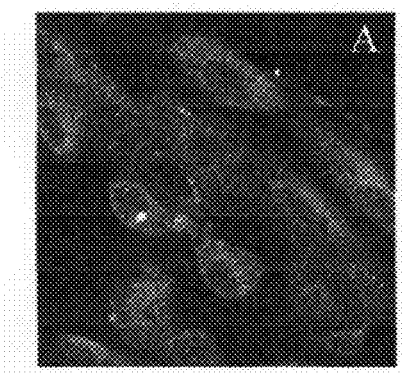
FIG. 2 is a photograph of cells isolated from human kidney papilla stained with E-cadherin, a cell junction protein antibody.
Figure 3:
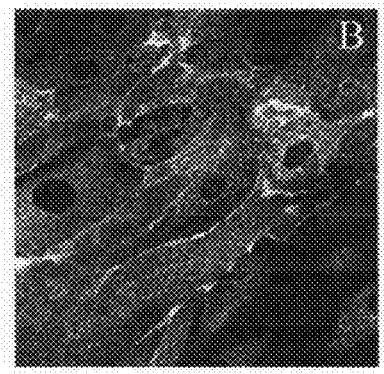
FIG. 3 is a photograph of cells isolated from human kidney papilla stained with N-cadherin, a cell junction protein antibody.
Figure 4:
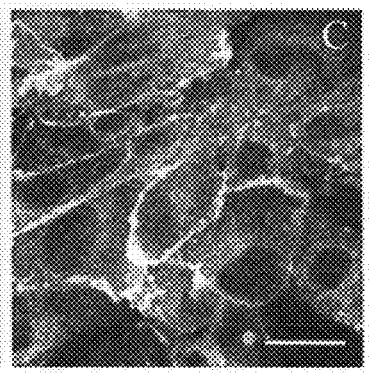
FIG. 4 is a photograph of cells isolated from human kidney papilla stained with Pad-cadherin, a cell junction protein antibody.
Figure 5:
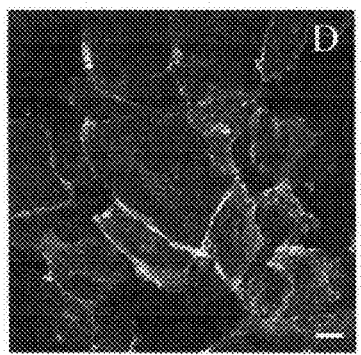
FIG. 5 is a photograph of cells isolated from human kidney papilla stained with β-catenin, a cell junction protein antibody.
Figure 6:
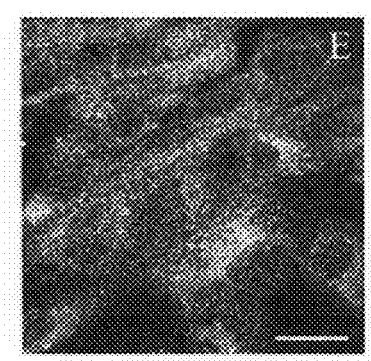
FIG. 6 is a photograph of cells isolated from human kidney papilla stained with Occludin, a cell junction protein antibody.

There is general agreement that adult stem cells should exhibit continuous self-renewal and the capacity to give rise to multiple differentiated cell lineages [3]. Consequently, stem cells have the unusual property of being able to undergo asymmetric cell division, wherein one progeny remains a stem cell and the second progeny is a non-stem cell sister or transient amplifying precursor that undergoes a finite number of divisions prior to giving rise to fully mature, differentiated cells. Asymmetric DNA strand segregation is believed to be a key component of asymmetric stem cell division and serves to reduce the potential for mutation introduced by errors during DNA replication [12]. As shown in FIG. 1, in this scenario the chromosomes segregate non-randomly such that the stem cell retains the original chromosome set, while the transient amplifying precursor receives the newly replicated DNA. Such immortal DNA strand cosegregation mechanisms have been shown to be operative in intestinal cells and in cultured cell lines overexpressing p53 [9, 13, 14]. Relatively straightforward microscopic and flow cytometry based assays have been developed to assess the asymmetric cell division properties of stem cells based on such non-random DNA strand segregation [14].

For example, one microscopic assay is based on quenching of the fluorescent Hoechst dye in the presence of DNA labeled by bromodeoxyuridine. When cells are dividing symmetrically and labeled with bromodeoxyuridine, followed by Hoechst dye, all cells exhibit uniformly quenched Hoechst fluorescence. In contrast, if the bromodeoxyuridine labeled cells undergo asymmetric division, the bromodeoxyuridine is lost from the stem cell population and these cells are subsequently brightly stained with Hoechst. The profile of bromodeoxyuridine label retention measured by flow cytometry several passages after labeling may also reveal a population of asymmetrically dividing cells. For example, if cells are dividing symmetrically, all progeny will exhibit uniform label dilution. If cells are dividing asymmetrically, a population of unlabeled cells is expected.

Non-differentiated pluripotent cells, participating in kidney regeneration, are expected to undergo major phenotypic transitions, analogous to those occurring during normal kidney development. The major difference being that in regenerating kidney, progenitor cells have to undergo the necessary developmental stages to form new tubules in the context of the adult, fully mature kidney. It is known that tubulogenesis involves the integration of many cellular processes, such as differentiation, polarization, shape change, proteolysis, growth, mitosis, regulated cell death, motility, adhesion, signaling, ion fluxes, cytoskeletal organization and membrane traffic [15]. Moreover, tubules can be formed by cells under different conditions and induced by different factors. To predict the behavior of non-differentiated pluripotent cells in adult kidney, 2D filter cultures and 3D in vitro tubulogenesis models may serve as useful experimental tools. Filter cultures enable optimal cell polarization in vitro and are useful for monitoring the acquisition of such epithelial hallmarks as apical and basolateral plasma membrane polarity and transepithelial resistance due to the presence of tight junctions [15]. At present, three-dimensional (3D) extracellular matrix gel culture (composed of collagen I) is widely used for in-vitro tubulogenesis studies [15]. This model provides an "in vivo-like" culture condition and represents a simplified model for true tissue/organ development.

An important and complicated stage in kidney repair is epithelial redifferentiation, which requires a mesenchyme-to-epithelium transition of progenitor cells, such as embryonic stem cells or dedifferentiated survivor cells. Growth factors, including insulin-like growth factor-1 (IGF-1), hepatocyte growth factor (HGF) and epidermal growth factor (EGF), in combination with matrix derived cues, most likely contribute to de-novo generation of tubular epithelia. The search for actual inducing signals that directly promote conversion of mesenchyme to epithelia is still in process. Wnt proteins (particularly Wnt4) were implicated to be essential for mesenchyme transition during tubulogenesis [16]. In addition, the soluble tubulogenic factors, such as leukemia inhibitory factor (LIF), transforming growth factor beta2 (TGF beta2), fibroblast growth factor 2 FGF2 (alone and in combination), were identified as the most striking inducers of renal cell differentiation [17-19]. The ability of the cells to respond to inductive signals depends on the expression of a number of renal specific transcription factors such as WTI and Pax2, among others [20, 21].

The key events in the recovery of renal tissue from injury are cell dedifferentiation, proliferation and subsequent redifferentiation back into fully polarized epithelial cells. Morphogenic processes that could occur during kidney reconstruction (mediated by dedifferentiated surviving cells or transplanted embryonic stem cells) would be highly dependent on the expression of proteins, implicated in renal tissue development. Among these, members of the cadherin superfamily are likely to play a critical role [10]. Several cadherins, such as E-cadherin, R-cadherin, cadherin-6, cadherin-1 1, N-cadherin and P-cadherin, are expressed during nephrogenesis [22]. In addition, the kidney-specific cadherin 16 has recently been implicated in the differentiation of adult stem-like cells from mouse kidney [23].

Cadherin-mediated adhesion is critical during embryogenesis, morphogenesis and in the normal function of epithelial tissues. Cadherins promote Ca2+-dependent cell-cell adhesion through hemophilic interactions with cadherins on neighboring epithelial cells [24,25]. Via their carboxy-terminal cytoplasmic tail, classical cadherins associate with cell cytoskeletal molecules. For example, E-cadherin, which is highly expressed in epithelia, associates with β-catenin and α-catenin to promote interaction with the actin cytoskeleton [25-27]. The E-cadherin/β-catenin complex plays a dual role. On the one hand, it stabilizes cellular adhesion through cytoskeletal attachment and on the other hand, the protein complex modulates signal transduction and consequently imparts gene expression and cell cycle control. During the process of mesenchyme-to-epithelium transition in kidney organogenesis, N-cadherin is replaced by E-cadherin [28]. Expression of different cadherins and so-called cadherin switches (when one of the cadherins is replaced by another member of the same cadherin protein family) is temporally and spatially regulated during kidney development. This precisely regulated expression is implicated in such critical stages as initial aggregation of mesenchymal cells, mesenchyme-to-epithelium transition, cell proliferation, migration, adhesion and other complex signaling events leading to the formation of mature nephrons.

In vivo animal studies have been used to complement in vitro differentiation analyses and provide critical information regarding the ability of stem cells to repopulate specific tissues. Bone marrow derived hematopoietic stem cells have been studied most extensively with animal studies being used to demonstrate pluripotency [29]. Thus, cells were shown to differentiate not only into the hematopoietic lineage, but also to give rise to epithelia of the liver, lung and gut. In the case of kidney, there is conflicting evidence as to the potential of circulating hematopoietic stem cells to contribute to renal repair [30, 31]. The most recent study suggests that increased cytokine levels enhance kidney recovery following ischemic injury by reducing inflammation rather than by increasing the incorporation of bone marrow derived cells into regenerated tubules [31]. The quest to identify and characterize kidney-derived stem cells has also relied on animal models. Rodent renal ischemic injury models have been used to provide evidence for a direct role of tubular epithelial cells in tubule regeneration [11], as well as to support the role of rodent papillary cells in kidney regeneration [1]. Stem cell transplantation with or without renal injury has in turn been used to monitor the capacity of the implanted cells to reintegrate within the intact kidney [1, 32]. In one such study, human CD133 positive cells were xenotransplanted to a SCID mouse following induction of renal ischemia by glycerol injection and the incorporation of the human cells into kidney tubules was scored [32]. At present, the nature and identity of the progeny of renal papillary cells in vivo remains an open question. On the whole, establishing the optimal conditions for induction of differentiation, as well as elucidating the requisite protein expression profiles involved in restoration of injured kidneys, is of particular importance for successful implementation of renal stem cell therapy. There are a number of potential therapeutic applications for stem cells in the future. One is the possible introduction of multipotent cells of different origins for replacement of damaged nephrons following renal injury and monitoring the regenerative process. Another is genetic modification of multipotent cells (stable expression of a selected protein) and their implantation into host renal tissues. This approach may offer improved control over indiscriminate direct injections of gene vectors [10]. The correction of genetic defects would be helpful for the treatment of inherited renal diseases, such as ADPKD. Further, cell therapy could be used as more direct approach for effective delivery of therapeutic drugs. Pluripotent cells, such as adult and embryonic stem cells or dedifferentiated kidney cells, have a rare natural capability of regenerating damaged tissue. Cell therapy will be one of the most advanced therapeutic tools in the nearest future. Tissue based therapy will also support presently used methods, such as kidney transplantation, where genetically modified pluripotent cells may contribute to minimizing immunologic rejection of the transplanted kidney.

As stated above, according to one embodiment, the present invention includes methods for the isolation of renal papillary cells and/or renal stem cells. Such cells may be isolated from one or more human kidneys. As used herein, the term "isolated" means that a cell population is removed from its natural environment. As used herein, the term "purified," means that a cell population is essentially free from any other cell type.

The cells of the present invention may be isolated from a region deep within the inner medullary region of the kidney. In situ in the kidney, the cells of the present invention may reside within the loops of Henle, the tubules found deep within the kidney papilla.

According to another embodiment, the present invention also includes isolated cells populations with a marker staining pattern similar to the marker staining pattern of isolated human renal papillary cells, wherein the cell populations are isolated from a cell source other than the renal papillary region of a human kidney. Such populations may be isolated, for example, from placental cord blood, bone marrow, embryonic stem cell populations, neonatal stem cell populations, and/or somatic stem cell populations. Such markers may include, but are not limited to CD133 and nestin.

According to yet another embodiment, the present invention also includes methods of culturing, co-culturing, maintaining and/or storing isolated human renal papillary cells so that further differentiation does not occur.

The isolated human renal papillary cells described herein may possess the ability to differentiate into specialized cells having one or more structural and/or functional aspects of a physiologic kidney. The present invention also includes methods of culturing, co-culturing maintaining and/or storing isolated human renal papillary cells so that differentiation occurs. For example, hypoxic conditions, ischemic injury, or conditions mimicking ischemic injury may be used to induce isolated human renal papillary cells to differentiate. As another example, the isolated human renal papillary cells may be co-cultured with other types of cells, such as differentiated adult human kidney tubule cells or embryonic neural stem cells. Accordingly, using various methods described herein, isolated human renal papillary cells may be induced to differentiate into different types of cells such as, for example, into tubular epithelial cells or neuronal cells. According to still another embodiment, the present invention also includes such populations of differentiated cells.

The isolated human renal papillary cells described herein possess the ability to differentiate into specialized cells having one or more structural and/or functional aspects of a physiologic kidney. For example, isolated human renal papillary cells may be induced to differentiate into, for example, tubular epithelial cells or may be used to repopulate kidney tubules.

According to another embodiment, the present invention also includes gene expression profiles of isolated human renal papillary cells. Such gene expression profiles may be used in the identification of markers for stem cells. Such gene expression profiles may be used for monitoring, for example, proliferative potential and differentiation status of stem cells. Such gene expression profiles include, but are not limited to, gene expression profiles from undifferentiated cell populations, gene expression profiles from differentiated cell populations, and gene expression profiles from cell populations obtained from individuals. Individuals from which gene expression profiles may be obtained include, but are not limited to, individuals with normal kidney function, individuals suffering from a kidney disorder, individuals suspected of carrying one or more genes for a heritable kidney condition, individuals undergoing treatment for a kidney disorder, and individuals undergoing treatments with nephrotoxic side effects. Gene expression profiles may be obtained by any known methods. For example, gene expression profiles may be obtained using the Human Genome U133 Plus 2.0 Genechip® Array (Affymetrix, Santa Clara, Calif.).

According to yet another embodiment, the isolated human renal papillary cells disclosed herein may be administered to a subject for the treatment of a kidney disorder. The cells to be administered include undifferentiated cells and/or cells that have been induced to differentiate.

According to some embodiments, the isolated human renal papillary cells disclosed herein may include an exogenous polynucleotide. According to some embodiments, the exogenous polynucleotide may encode a therapeutic agent. According to another embodiment, the exogenous polynucleotide may include an expression vector.

According to a still further embodiment, the isolated human renal papillary cells of the present invention may be used in bioartificial kidneys such as, for example, the bioartificial kidney described in U.S. Pat. No. 6,150,164.

Those of skill in the art will be familiar with a wide variety of materials and methods that are suitable for use to perform the methods described in the present disclosure. For example, suitable materials and methods include, but are not limited to those described in U.S. Pat. Nos. 5,429,938; 6,060,270; 6,150,164; 6,410,320; and 6,458,588; and U.S. Patent Application Serial No. 20020119566 A1.

As stated above, according to one embodiment of the present invention, a potential adult stem cell population has been isolated and characterized from human kidney papilla. The cells occupy a niche that is deep within the inner medulla and relatively hypoxic providing protection against oxidative stress. Preliminary ultrastructural analyses show these cells in situ exclusively in the loops of Henle of tubules found deep within the kidney in papilla. The cells are embedded between the tubular epithelia and have a characteristic morphology with large nuclei and a limited cytoplasm that is readily distinguishable from that of tubular epithelial cells. These putative adult human renal stem cells express markers that are characteristic of stem cells, including CD133 and nestin. In the presence of serum or specific growth factors the cells are able to adopt tubular epithelial-like or neuronal-like phenotypes. In vitro studies show the papillary cells readily associate with cortical tubular epithelia, both on filter cultures and in 3D collagen gel cultures, and in serum-free, 2D cultures form structures resembling neurospheres.

Various methods for demonstrating that a subpopulation of human papillary cells constitutes adult renal stem cells that can differentiate into tubular epithelia are described below. Methods for characterizing isolated human papillary cells for their self-renewal potential, ability to give rise to tubular epithelia and their ability to repopulate kidney tubules are also described. At present there is limited information about the origin and identity of adult renal stem cells, making the work highly relevant for the development of tissue engineering and alternate renal tissue repair strategies.

Self-Renewal Potential and Asymmetric DNA Segregation

Two hallmarks ascribed to bona fide stem cells is their ability to undergo indefinite self-renewal and asymmetric DNA strand segregation. To assay self-renewal potential, primary human papillary cells can be maintained in culture under conditions designed to maximize the maintenance of undifferentiated multipotent adult progenitor cells. The cells can be continuously cultured and passaged prior to confluence. By measuring the cell number at each passage and monitoring the number of passages we can establish if renal papillary, CD133 and nestin positive cells can be maintained in culture long-term, for example, logarithmic growth for up to one year. Cells can be screened by flow cytometry for various markers of cell differentiation at the start and at defined intervals. Microscopic and flow cytometry based assays can be used to assess the potential for asymmetric DNA segregation. These studies enable the distinction between isolated human papillary cells that resemble a bona fide stem cell population and cells that are transient amplifying precursor cells.

Pluripotent Phenotype and Ability to Differentiate into Tubular Epithelia

A third hallmark ascribed to stem cells is the ability to give rise to cell populations with various differentiated phenotypes. In vitro cell differentiation assays can be used to characterize the potential of the isolated papillary cells to yield distinct cell populations with a particular emphasis on their ability to differentiate into tubular epithelia. In vitro, 2D filter cultures and 3D extracellular matrix gel systems are widely used to study renal tubule epithelial cell function. Epithelial cells grown on 2D filter cultures form cellular junctions and establish a transepithlial resistance. Epithelial cells, grown in 3D collagen gel cultures, form complex cyst-like or tubule-like epithelial structures. 2D and 3D cell cultures supplemented with select growth factors or tubulogenic factors can be studied as a function of time. To assess differentiation status, cell morphology, expression of differentiation specific markers, transepithelial resistance and tubulogenesis can be analyzed. Once a bona fide renal stem cell population is identified, a renal stem cell gene expression profile can be established relative to fully differentiated tubular epithelia to facilitate future stem cell isolation and characterization. Studies monitoring the differentiation potential of human papillary progenitor cells can provide insights into the possible utility of these cells in renal tubular epithelial tissue regeneration.

Contribution to Tubular Regeneration

A fourth hallmark ascribed to stem cells is in vivo regenerative capacity following renal injury. Such analyses necessitate animal studies. Pilot studies can be performed with xenotransplanted, immunosuppressed rats to evaluate the optimal model for in vivo functional analyses of the differentiation and regenerative potential of the putative human papillary stem cells. The incorporation of labeled human cells into various tubules versus the kidney parenchyma can be quantified, as can the dependence on renal injury for incorporation. An optimal animal model system can thus be defined, laying the foundations for more detailed animal studies.

Various embodiments of the present invention are illustrated by the following examples. It is to be understood that the particular examples, materials, amounts, and procedures are to be interpreted broadly and as non-limiting. Accordingly, it will be appreciated that while may of the examples included herein describe the use of specific instruments, assay reagents, assay systems, material sources, etc., those of skill in the art will be familiar with many instruments, assay reagents, assay systems, material sources, and the like, which will or could be used for the same purposes. Accordingly, such description is intended to be exemplary in nature and should not be interpreted as limiting the invention to any of the specifically described instruments, assay reagents, assay systems, material sources etc.

Example 1

A Method for Identifying a Stem Cell Population in Human Renal Papilla with the Capacity to Differentiate into Neuronal- and Epithelial-Like Lineages Cells and Culture We have isolated and characterized cells isolated from renal papilla of three different human kidneys not suited for transplant. Tissue was obtained through the National Disease Research Interchange (NDRI) and the protocol has been judged as exempt by the institutional HRRC. The kidney is bisected and renal papilla are dissected out. The papillary cells are disaggregated using a cocktail of enzymes (including collagenase, hyaluronidase, DNAase I, and soybean trypsin inhibitor) in DME/F12 medium. Digestion is performed at 3% for 60 minutes with vigorous intermittent vortexing. Following digestion, the cells are collected by centrifugation and resuspended in Renal Epithelial Cell Basal Medium (REBM, Clonetics/Biowhittaker, CC-3 191) containing growth factor supplements, cultured for 1-2 passages, and frozen. Individual frozen aliquots of these cells can readily be thawed and cultured in excess of the 4-6 passages that is normally the in vitro limit for cortical tubular epithelial cells. For efforts to purify the CD133 positive cells using magnetic cell separation methods with a CD133 antibody conjugated to commercially available magnetic bead have been used (see Example 2 below), cells are suspended in EDTA/PBS and bound cells are cultured directly after isolation in REBM The isolated human papillary cells were characterized in vitro using immuno-fluorescence methods and based on initial evaluations appear comparable to those isolated by Al-Awqati and colleagues from rodent papilla and reported to represent adult renal stem cells [1]. Both the rodent and human cells occupy a specialized niche that is deep within the inner medulla and protective against oxidative stress. Our preliminary ultrastructural analyses on the human CD133 positive, nestin positive cells show these cells in situ are exclusively in the loops of Henle of tubules found deep within the kidney in papilla. The cells are embedded between the tubular epithelia and have a characteristic morphology that is readily distinguishable from that of tubular epithelial cells. These putative adult human renal stem cells express markers that are characteristic of stem cells, including CD133 and nestin. In the presence of serum or specific growth factors the cells are able to adopt tubular epithelial-like or neuronal-like phenotypes. The papillary cells readily associate with cortical tubular epithelia, both on filter cultures and in 3D collagen gel cultures. We have previously cultured and characterized primary renal epithelial cells, isolated from normal human kidneys and characterized the deficits in cell polarity associated with primary human autosomal dominant polycystic kidney disease (ADPKD) cells. [33-36] Moreover, we have previously demonstrated that ADPKD cells exhibit a partially dedifferentiated mesenchymal-like state as evidenced by altered cystogenic versus tubulogenic potential, changes in cell-cell adhesion and signaling microdomains.

Phenotypic Characteristics of Human Papillary Cells in Culture

Figure 7:
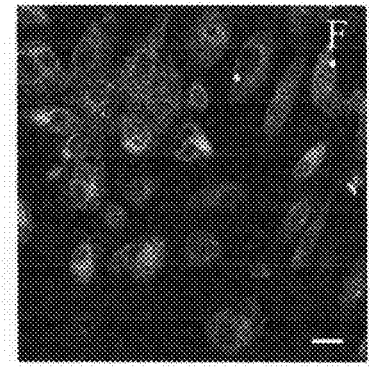
FIG. 7 is a photograph of cells isolated from human kidney papilla stained with Nestin, a neuronal stem cell marker.

Isolated human papillary cells developed an immature epithelial-like phenotype and their shape was similar to the shape of primary human kidney epithelial cells when cultured in serum and for 3-4 days on plastic dishes. The cells lacked tight junctions, but formed adherens, junctions composed of the mesenchymal adhesion molecule N-cadherin and beta-catenin and most likely another cadherin, based on the strong staining with a pan-cadherin antibody. See FIGS. 2-6. Cadherin-6 (K-cadherin) and adhesion molecule N-cam are most likely not involved in papillary cell differentiation since they were not expressed at the cell-cell adherens junctions. The cells remained slightly positive for the neuronal stem cell marker nestin (FIG. 7), though its expression was highly sensitive to changes in culture conditions. Nestin expression was highest when cells were less differentiated as in serum free medium and decreased with time in culture. Overall the traits of the renal papillary cells are quite distinct from those we have described for mature renal tubular epithelial cells [34,35].

Figure 8:
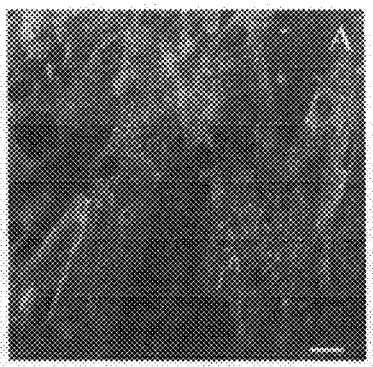
FIG. 8 is a photograph depicting human papillary cells grown in sedrum-free media with EGF stained with N-cadherin.
Figure 9:
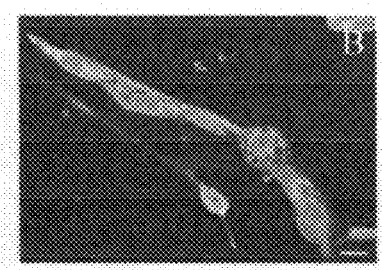
FIG. 9 is a photograph depicting human papillary cells grown in sedrum-free media with EGF stained with Nestin.
Figure 10:
FIG. 10 is a photograph depicting human papillary cells grown in sedrum-free media with EGF stained with Nestin.
Figure 11:
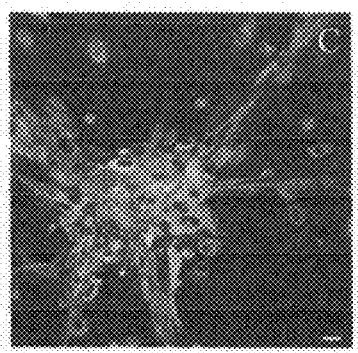
FIG. 11 is a photograph depicting human papillary cells grown in sedrum-free media with EGF stained with Nestin.
Figure 12:
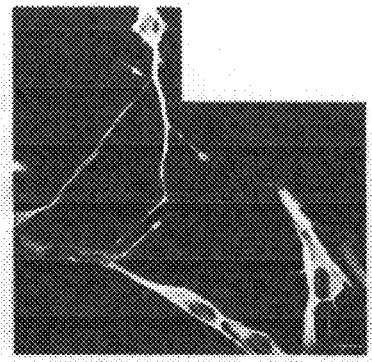
FIG. 12 is a photograph depicting human papillary cells grown in sedrum-free media with 20 ng·ml EGF stained to show expression of the neuronal specific marker beta III tubulin.
Figure 13:
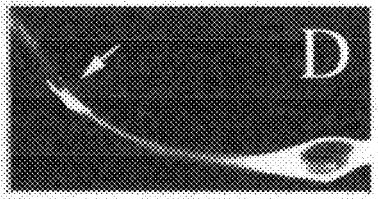
FIG. 13 is a photograph depicting human papillary cells grown in sedrum-free media with 20 ng·ml EGF stained to show expression of the neuronal specific marker beta III tubulin.

The phenotype of rodent papillary cells was sensitive to the content of serum in the media. Similar to rodent cells, the human papillary cells exhibited dramatic changes in cell shape when grown in serum-free medium. Following 3-4 days in serum-free media the cells became highly elongated and spindle-shaped. See FIGS. 8-13. The expression of N-cadherin decreased (FIG. 8), whereas expression of nestin increased and the cells developed a neuronal-like shape (FIGS. 9, 10). Seven days after seeding, the human papillary cells formed cellular aggregates (FIG. 11) and structures resembling neurospheres often used to characterize stem cell origin (not shown). Differentiation into neurosphere-like structures occurred synchronously across the culture when cells were grown on filter supports above embryonic neural stem cells of rodent origin. When grown in serum free medium supplemented with EGF the cells became positive for the neuronal marker beta III tubulin and appeared to 'synapse' with each other (FIGS. 12, 13). Analogous shape changes, as well as the formation of aggregates/spheres were described for the rodent papillary cells under serum fee conditions. Long-term culture also induced shape changes, with cells becoming spindle-shaped and growing on the top of the initial monolayer (this phenomenon was also observed in rodent papillary cells).

Figure 14:
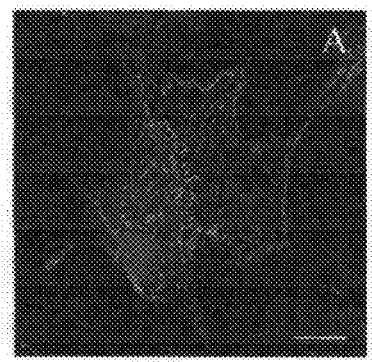
FIG. 14 is a photograph of human papillary cells loaded with CFDA fluorescent green dye, mixed with cortical epithelial cells from the same kidney and stained for cholesterol using a red dye.
Figure 15:
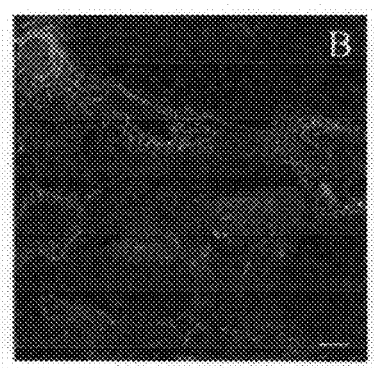
FIG. 15 is a photograph of human papillary cells loaded with CFDA fluorescent green dye, mixed with cortical epithelial cells from the same kidney and stained for cholesterol using a red dye.
Figure 16:
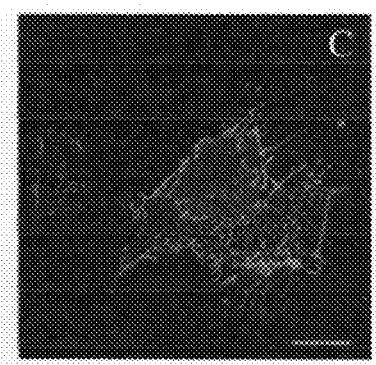
FIG. 16 is a photograph of human papillary cells loaded with CFDA fluorescent green dye, mixed with cortical epithelial kidney cells from a different patient and stained for cholesterol using a red dye.
Figure 17:
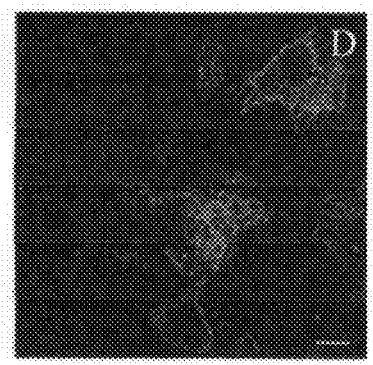
FIG. 17 is a photograph of human papillary cells loaded with CFDA fluorescent green dye, mixed with cortical epithelial kidney cells from a different patient and stained for cholesterol using a red dye.

The potential for interactions between cells from kidney papilla and normal cortical kidney epithelial cells were also evaluated. The isolated papillary cells were first loaded with green fluorescent dye 5(6)-CFDA (Molecular probes) and then mixed with cortical kidney epithelial cells from the same patient and with the cells from a different patient. After three days in culture, the cells were stained with monomeric PFO (binds cholesterol) to outline cell membranes. Papillary cells were consistently seen incorporated within the mixed population cell monolayer and made contacts both with the cortical epithelial cells from the same patient (FIGS. 14, 15) and with cells derived from a different patient (FIGS. 16, 17).

In Vitro Renal Tubulogenesis in 3D Collagen Gel Cultures

Figure 18:
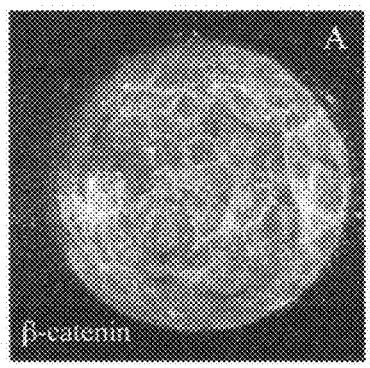
FIG. 18 is a photograph depicting the growth of cortical human tubular epithelial cells grown alone, fixed, and stained with β-catenin.
Figure 19:
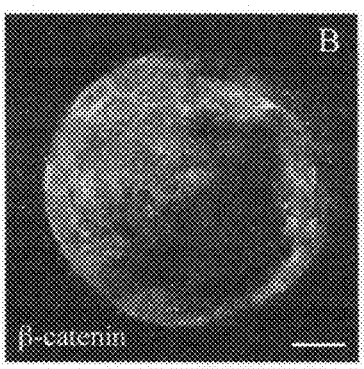
FIG. 19 is a photograph depicting the growth of cortical human tubular epithelial cells grown in combination with CFDA-labeled papillary cells, fixed, and stained with β-catenin.
Figure 20:
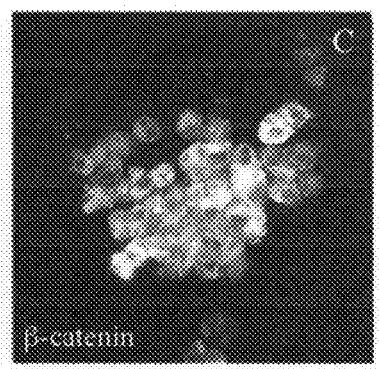
FIG. 20 is a photograph depicting the growth of cortical human tubular epithelial cells grown alone in 3D collagen gels for 10 days, fixed, and stained for β-catenin.
Figure 21:
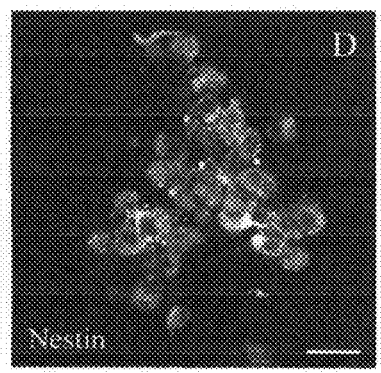
FIG. 21 is a photograph depicting the growth of cortical human tubular epithelial cells grown alone in 3D collagen gels for 10 days, fixed, and stained for Nestin.

The final outcome of complex events, associated with cell differentiation, is a functional three-dimensional organization of cells into structures and organs. Extracellular matrix (ECM) gels are widely used to study epithelial cell morphogenesis. This three-dimensional culture system provides a model that mimics the "in vivo" environment in which cells grow and differentiate. Cells plated in ECM gel (e.g., collagen gel) migrate, proliferate, differentiate and eventually form hollow spheres [15]. In preliminary studies, both primary kidney epithelial cells from the cortex and cells isolated from human papilla were mixed with collagen-1 gel (prepared according manufacturers instructions) and plated in 24 well cell culture dishes. After 10 days in collagen gels, primary kidney epithelial cells formed complex hollow cyst-like epithelial structures with intact adherens junctions shown by the honey-comb-like beta-catenin staining (FIG. 18). Cells from human papilla formed aggregates of loosely attached round cells, positive for nestin and intracellular beta-catenin when cultured alone, but were readily incorporated into spheres with budding tubules when cocultured with epithelial cells (compare FIGS. 19 to 20 and 21). Matrix components secreted by renal epithelia can have profound effects on the differentiation status of epithelial cells in culture [19, 37] as can supplemental growth factors. For these initial studies, no supplemental growth factors were added to the collagen cultures. However supplemental growth factors and alternate matrices (for example, Matrigel, collagen IV, and laminin) could be used to define the conditions that support the differentiation of papillary cells in vitro.

CD133 and Nestin Positive Cells are Associated with Loops of Henle

CD133 is also known as prominin-1 and was originally identified in neuroepithelial stem cells [38,39]. CD133 is a pentaspanning, cell surface glycoprotein with an extracellular N-terminus and intracellular C-terminus. The exact function of CD133 is unknown, but its association with primitive hematopoietic stem and developing epithelium, have prompted its wide use to identify stem cell populations. Staining of isolated human papillary cells revealed a subset of cells that were strongly stained with a rabbit polyclonal anti-CD133 antibody directed against a unique C-terminal peptide (Abcam Ltd.). The same cells were also nestin positive. Based on the staining properties of the isolated cells, we stained tissue sections taken from various parts of the kidney, including the cortex, medulla and papilla, for nestin (mouse monoclonal antibody specific for human nestin, Chemicon) and CD133. Staining for beta-catenin, Tamm-Horsfall antigen and various lectins served as markers to discern the identity of individual tubule segments. Strikingly, cells expressing both nestin and CD133 were exclusively localized to papillary loops of Henle (identified by the presence of Tamm-Horsfall antigen) (FIGS. 22-26).

Figure 22:
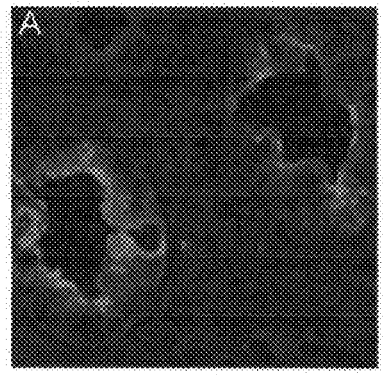
FIG. 22 is a photograph of cryosections derived from the medulla of a normal human kidney, fixed and immunostained for Tamm-Horsfall antigen (red) and nestin (green).
Figure 23:
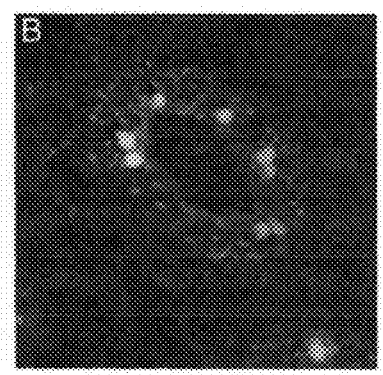
FIG. 23 is a photograph of cryosections derived from the papilla of a normal human kidney, fixed and immunostained for Tamm-Horsfall antigen (red) and nestin (green).
Figure 24:
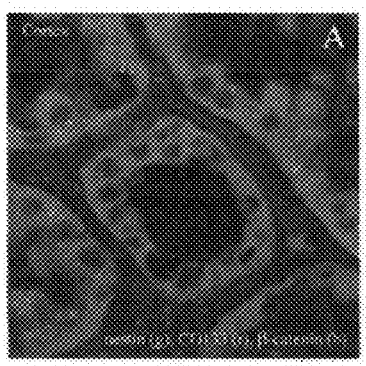
FIG. 24 is a cryosection from human kidney cortex, fixed and immunostained for nestin (green), CD133 (red) and β-catenin (blue). The nuclei are unstained.
Figure 25:
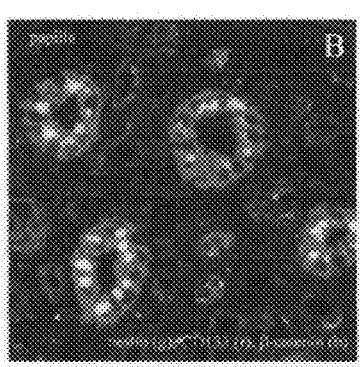
FIG. 25 is a cryosection from human kidney papilla, fixed and immunostained for nestin (green), CD133 (red) and β-catenin (blue). The nuclei are unstained.
Figure 26:
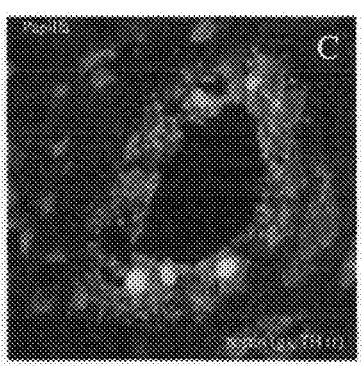
FIG. 26 is a cryosection from human kidney papilla, fixed and immunostained for nestin (green) and Tamm-Hosfall antigen (red). The nuclei are identified by Hoechst staining.
Figure 27:
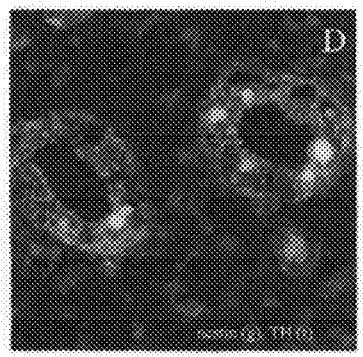
FIG. 27 is a cryosection from human kidney papilla, fixed and immunostained for nestin (green) and Tamm-Hosfall antigen (red). The nuclei are identified by Hoechst staining.
Figure 28:
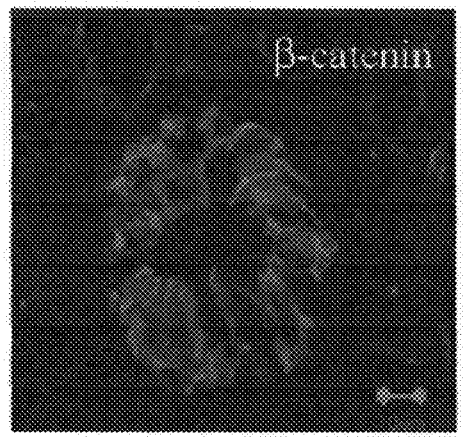
FIG. 28 is a composite projection of cryosections from single human kidney cortex tubules fixed and immunostained for β-catenin imaged at 0.4 μm intervals and viewed in the x-y direction.
Figure 29:
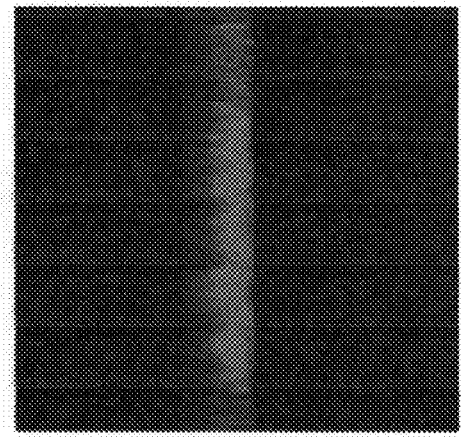
FIG. 29 is the composite projection of FIG. 28 viewed in the x-z direction.
Figure 30:
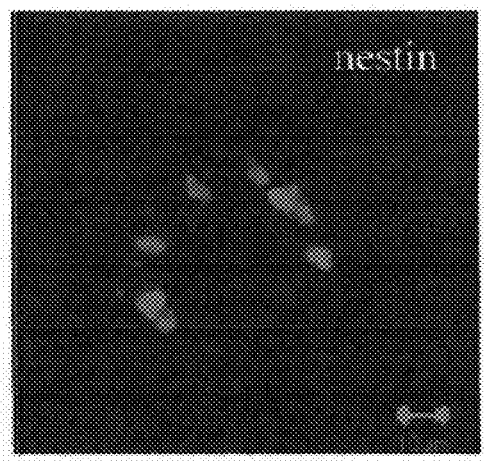
FIG. 30 is a composite projection of cryosections from single human kidney cortex tubules fixed and immunostained for Nestin imaged at 0.4 μm intervals and viewed in the x-y direction.
Figure 31:
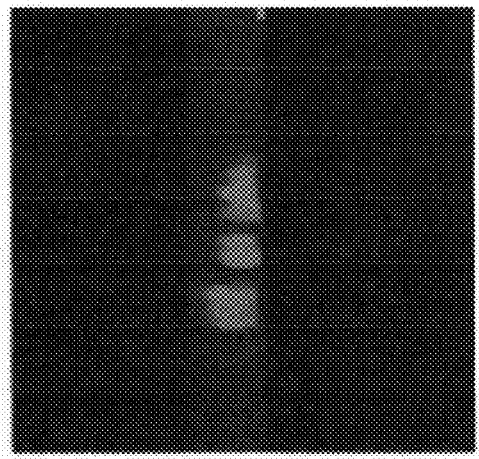
FIG. 31 is the composite projection of FIG. 30 viewed in the x-z direction.
Figure 32:
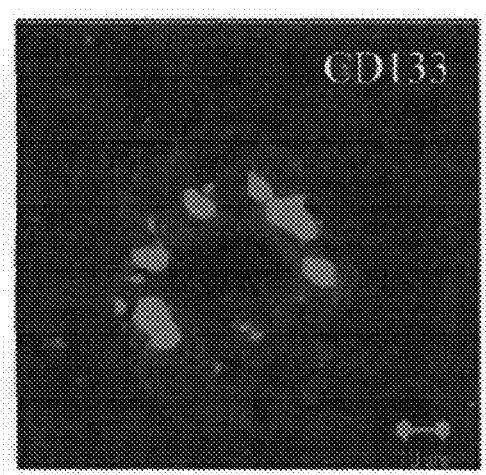
FIG. 32 is a composite projection of cryosections from single human kidney cortex tubules fixed and immunostained for CD133 imaged at 0.4 μm intervals and viewed in the x-y direction.
Figure 33:
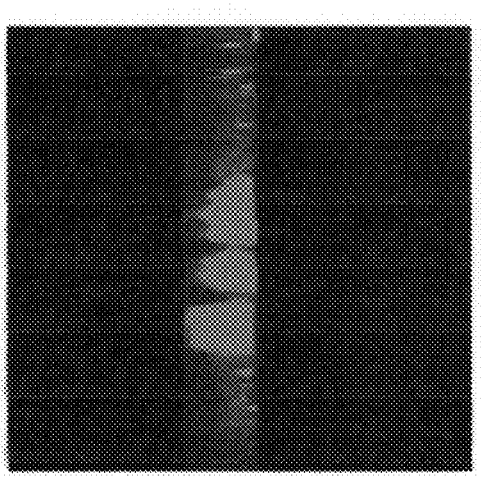
FIG. 33 is the composite projection of FIG. 32 viewed in the x-z direction.
Figure 34:
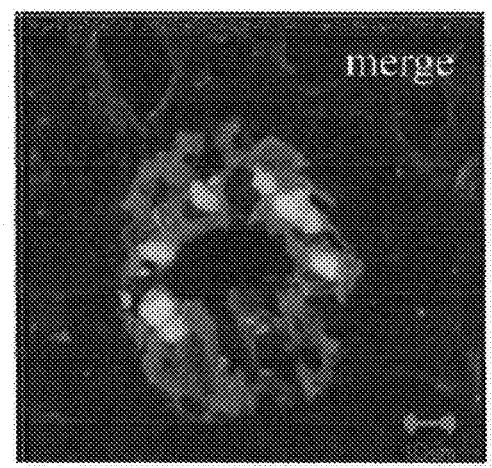
FIG. 34 is a composite projection of cryosections from single human kidney cortex tubules fixed and imaged at 0.4 μm intervals and viewed in the x-y direction.
Figure 35:
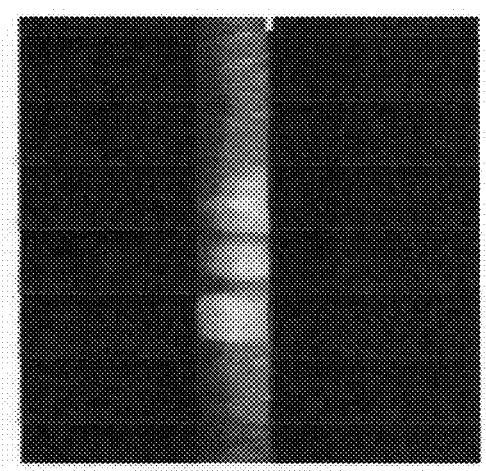
FIG. 35 is the composite projection of FIG. 28 viewed in the x-z direction.

At first glance, the staining appeared to label only the nucleus of small cells embedded between the tubular epithelia (FIGS. 22, 23). However, more detailed analysis using Hoechst staining and confocal x-z and stacked x-y images showed these cells to be fully integrated in the tubular epithelial layer (FIGS. 24-35).

Ultrastructural Analyses Reveal a Unique Cell Type

Figure 36:
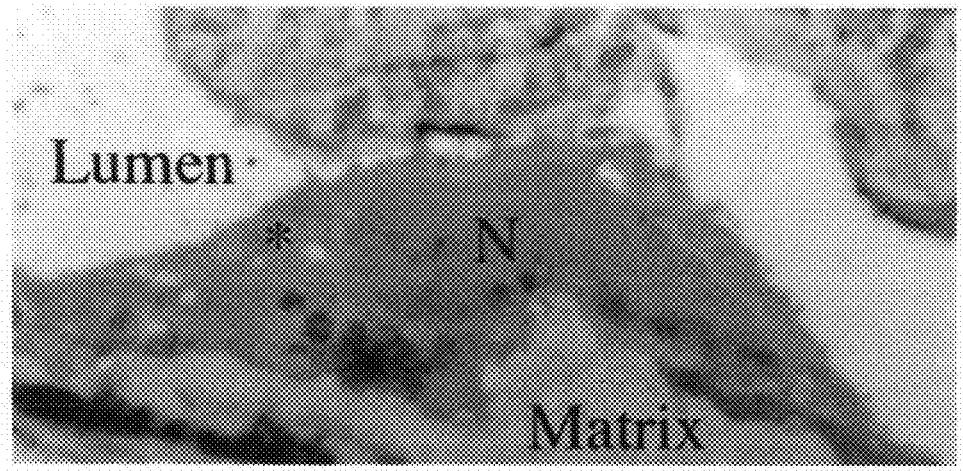
FIG. 36 is a photograph of cryosection of human renal papilla imaged on a Hitachi 7500 transmission electron microscope at 6,000×.
Figure 37:
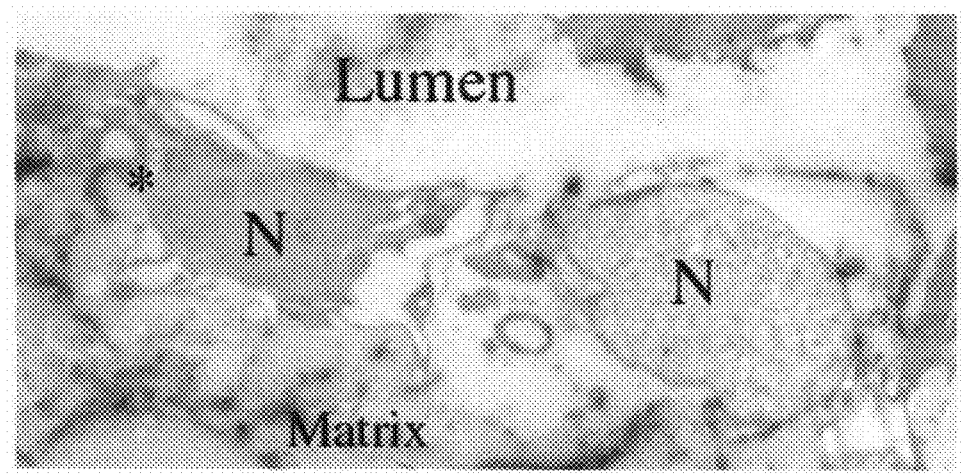
FIG. 37 is another photograph of cryosection of human renal papilla imaged on a Hitachi 7500 transmission electron microscope at 6,000×.

Electron microscopic analysis of cryosectioned kidney tissue identified a population of morphologically distinct cells with a large nucleus and a thin rim of cytoplasm in the papillary tubules (FIGS. 36, 37). These cells were not seen in the medulla or the cortical tubules. Based on the fact that the cells have few microvilli, are not especially cuboidal and exhibit a highly interdigitated association with the underlying matrix, they appear to be distinct from intercalated cells of the collecting duct.

The methods described in this example can be used to identify a stem cell population in human renal papilla with the capacity to differentiate into neuronal- and epithelial-like lineages. Example 2, below, provides methods to further characterize this adult renal stem cell population for use in the advancement of alternative renal repair strategies.

Example 2

Methods for Characterization of Adult Renal Stem Cell Populations Cells and Cell Culture Human primary epithelial (NK) cells, obtained from previously healthy individuals, are already available in the laboratory. NK renal epithelial cells are derived from the cortex of kidneys not suited for transplant (obtained through the National Disease Research Interchange). Cells are isolated by finely mincing the cortex and releasing cells by enzymatic digestion in a cocktail of collagenase, hyaluronidase, DNase I, soybean trypsin inhibitor and DMEM/F12 media as described in more detail in Example 1 [35, 40, 41]. Human renal papillary cells can be isolated by bisecting the human kidney slightly off-center and scooping out the papilla (5-6 per kidney). The papillary cells can be isolated and cultured. Briefly, the cells are released by enzymatic digestion as described for the cortical epithelial cells and pelleted by centrifugation. The cells are plated in DMEM/F12 media with or without serum or in renal epithelial cell growth media (Clonetics, Walkersville, Md. containing low serum, 10 ng/ml epidermal growth factor, 1 ml/l epinephrine, 5 mglml insulin, 6.5 pglml triiodothyronine, and 10 mg/ml transferrin). We obtain one confluent T 25 $cm^2$ flask of cells from the first plating. The cells may be expanded or frozen and stored. We have not observed a loss in cell viability or differentiation potential caused by freeze thawing. Cells can be grown in 2D cell culture conditions, on plastic (solid) or 0.4 µm pore filter (permeable) supports (Falcon Becton Dickinson) or in 3D collagen gel culture. Supplemental growth factors (HGF, EGF, human LIF, TGF-P) and alternate matrix components (laminin, Matrigel, collagen IV) and coated filters are readily available from commercial sources. Hypoxic conditions, resembling those present in papilla in vivo, may influence the survival and differentiation potential of stem cells [42, 43]. Accordingly, incubators suitable for culture under hypoxic conditions may be used if necessary.

To confirm the consistency of results generated from these experiments, renal papillary cells from any number of patients, such as 6-8, can be isolated and analyzed. Moreover, these patients may represent both genders and different ethnic and racial backgrounds. A collection of normal cortical tubular epithelial cells may be used as control samples.

Purification of CD133 Positive Subpopulation

Human papillary cells expressing the stem cell marker CD133 can be further purified as necessary by established immunoisolation protocols. To do so, cells are trypsinized and dispersed as a single cell suspension by passage through a 30 µm nylon mesh. Cells are chilled and incubated on ice with CD133 coated magnetic microbeads (Miltenyi Biotech) for 30 minutes. An FcR blocking solution is included during the incubation to reduce non-specific binding. A special column is placed in a magnetic holder and the cells bearing surface bound magnetic microbeads are retained. The column is rinsed and finally the retained cells are flushed through by removing the column from the magnetic stand. The magnetic beads are degradable and non-toxic. Therefore, the isolated cells can be cultured directly following isolation.

Animal Models

Wistar albino male rats or SOD mice lacking immune system function can be used for pilot animal studies to establish the optimal model for assaying the in vivo differentiation potential of putative human papillary stem cells, as previously described.

Self Renewal Potential and Asymmetric DNA Segregation

Continuous Long-Term Growth and Stem Cell Marker Assessment

Papillary cells can be freshly isolated from donated human kidneys obtained through the NDRI. The cells can be continuously cultured and passaged prior to confluence. At each passage the cell number can be determined by counting using a hemocytometer and recorded as described for bone marrow mesenchymal cells [29]. The total cell number and maximal number of passages can be determined. To date we have used the same media for our cortical epithelial cells and for the isolated papillary cells. If the media designed for mature differentiated cells proves to be inappropriate for the long-term maintenance of potential renal stem cells in culture, an expansion medium used successfully for bone marrow mesenchymal stem cells and for renal progenitor cells can be used [29,32]. In addition, a mesenchymal stem cell medium (SAFC Pharma, division of Sigma Aldrich) can be used. SAFC Pharma has made a significant investment in the development of media for improved stem cell culture and formulations used to promote hematopoietic stem cell amplification are already being tested in clinical trials.

Flow cytometry can be used to score for specific marker expression at the start and at periodic intervals during the long-term culture to evaluate the homogeneity and stability of the cell phenotype. The cells can be scored for the expression of specific mesenchymal stem cell markers such as CD133, CD731SH321 CD44, and CD29, as well as for human MHC I. We expect the cells to be negative for markers of hematopoietic markers such as CD34 and CD45.

With this example, long-term culture conditions for isolated renal papillary cells can be established. Hematopoietic stem cells have been maintained in continuous culture for up to one year without a change in logarithmic growth or phenotype [29]. Therefore, if the papillary cells are bona fide adult renal stem cells they should exhibit long-term continuous self-renewal potential and a stable phenotype. If the papillary cells fail to proliferate after a limited number of passages, the culture conditions can be modified to promote increased stem cell survival.

Asymmetric DNA Strand Segregation

The ability of cells to undergo asymmetric cell division is a key hallmark of stem cells. Asymmetric DNA strand segregation may be used as a measure of asymmetric cell division. A microscopic assay based on the quenching of the fluorescent Hoechst dye in the presence of DNA labeled by bromodeoxyuridine CAN be employed to monitor asymmetric DNA strand segregation [14]. Actively growing papillary cells cultured in non-differentiating expansion medium can be labeled with 0.5 pmol/L bromodeoxyuridine for 24 hours. The cells can subsequently either be fixed immediately or washed to remove the bromodeoxyuridine and cultured in serum containing media or in the presence of growth factors to induce differentiation. Normal cortical tubular epithelial cell cultures can be used as a control for symmetric strand segregation. Following fixation with ice-cold methanol the cells can be stained with the fluorescent Hoechst dye (332.58) and analyzed by epifluorescence microscopy on a Zeiss Axioskop equipped with a UV filter set.

When cells are dividing symmetrically and labeled with bromodeoxyuridine, followed by Hoechst dye, all cells are expected to exhibit uniformly quenched Hoechst fluorescence. In contrast, if the bromodeoxyuridine labeled cells undergo asymmetric division, the bromodeoxyuridine will be lost from the stem cell population and these cells will appear brightly stained with Hoechst. The numbers of brightly labeled cells can be quantified by counting several hundred cells under low power. The capacity of renal papillary cells to undergo asymmetric DNA segregation can be established by comparison with normal cortical tubular epithelial cell cultures. In the event that it is difficult to count large enough numbers of cells microscopically, a flow cytometry based assay where it is straightforward to count 10,000-100,000 cells within minutes can be used. The profile of oromodeoxyuridine label retention can be measured by flow cytometry several passages after labeling. If cells are dividing symmetrically, all progeny will exhibit more or less uniform label dilution. If cells are dividing asymmetrically, a population of unlabeled cells is expected. If papillary cell heterogeneity is an issue, CD133 enriched cells can be used.

The methods described in this example can be used to establish that isolated human renal papillary cells have two key hallmarks of stem cells, namely, the capacity to undergo indefinite self-renewal and asymmetric cell division.

Pluripotent Phenotype and Ability to Differentiate into Tubular Epithelia

Adult renal stem cells isolated from rodent papilla are myofibroblast-like and spindle-shaped and can express mesenchymal (alpha-smooth muscle actin), neuronal (nestin) and epithelial proteins (tight junction protein ZO-1) [1]. Thus, these cells exhibit pluripotent characteristics. The renal papillary cells isolated from human kidney in our laboratory, exhibit properties that are very comparable to those reported for the rodent papillary cells suggested to be adult kidney stem cells. Example 1 has documented the capacity of the renal papillary epithelial cells to adopt a neuronal-like phenotype (See, e.g., FIGS. 8-13). To further document the pluripotent phenotype of human papillary cells, methods for evaluating their capacity to differentiate into tubular epithelia using 2D and 3D culture systems by varying added growth factors and matrix components can be employed. Genomic fingerprints of renal stem cells and differentiated cell populations can also be established to facilitate future analyses and identification.

2-D Filter Culture Systems to Evaluate Epithelial Differentiation Capacity

Human renal papillary cells grown in culture in the presence of serum display a tubular epithelial phenotype with cell surface expression of N-cadherin and β-catenin. In an effort to trigger a more complete differentiation of putative adult kidney stem cells, cells can be cultured on filter supports and the influence of added growth factors and different matrix components tested. Known differentiation inducing factors can be added individually or in combination to renal epithelial cell culture media (lacking EGF). The appropriate concentrations of growth factors, such as hepatocyte growth factor. (HGF); soluble tubulogenic factors, such as leukemia inhibitory factor, (LIF), transforming growth factor (TGF) beta2, and fibroblast growth factor (FGF2), can be added in different combinations to cell culture media, for example, at a starting concentration of 10-20 ng/ml). These factors have all been implicated in kidney cell differentiation [17, 18]. Filter supports coated with fibronectin, collagen IV, collagen I, laminin or Matrigel (derived from Engelbreth-Holm-Swarm mouse sarcoma, BD Biosciences) can also be tested to evaluate the contribution of different matrices known to impact kidney cell differentiation [19, 37]. Precoated filters are commercially available. The cells can be plated at subconfluence and gown on 0.4 ym filter, supports. Samples can be analyzed at different time points (e.g., 3, 6, 12, 24 and 72 hours) following plating in culture. When grown on porous filter support, cultured epithelial cells can obtain nutrients from both basolateral and apical surfaces and adopt a highly differentiated and polarized phenotype, as compared to cells grown on solid plastic supports.

Suitable methods including immunofluorescence and biochemical methods can be used for a full analysis of differentiation-induced changes. The details of immunofluorescence as well as immunoblotting procedures are described for example, in [33-35]. The imaging can be performed on a Zeiss LSM510 confocal imaging system. We can score the expression and localization of tight junction proteins (Z01 and occludin), adherens junction proteins (E-cadherin, N-cadherin and B-catein), desmosomes (desmoglein, desmocollin and desmoplakin) and intermediate filament proteins (vimentin and cytokeratin). Fully formed junctions and the expression of cytokeratin are hallmarks of fully polarized and differentiated tubular epithelia. Tight junction function can be assessed by measuring transepithelial resistance and domain selective biotinylation using known methods such as those previously described by us in [35]. Markers for tubular epithelia of different renal segments can also be evaluated. Initially, *Lotus tetragonolobus* purpurea can be used for proximal; *Dolichos bioflorus* for distal; Tamm-HorsfoH antigen for loop of Henle. Other, more specific protein markers of proximal and distal tubules, can be used as appropriate (e.g., thiazide sensitive NaCl co-transporter, aquaporin-2, alkaline phosphatase, etc.). Finally, domain selective biotinylation and analysis of the overall apical and basolateral protein profiles can be used to assess the capacity of cells to polarize cell surface proteins [33,35]. Normal cortical tubular epithelial cells can serve as a positive control for these experiments.

Electron microscopy studies can also be conducted. Ultrastructural evaluation is useful for assessing the structures of cell junctions and details of cell morphology, e.g. presence of microvilli, columnar versus squamous phenotype, etc. Such information in conjunction with immunofluorescence staining for renal segment markers as detailed above can be informative for determining if different epithelial cell types are formed from renal papillary cells in culture. Established methods can be used for pre-embedment labeling with immunogold conjugates [44, 45]. The cells grown on cell culture filter inserts can be fixed (4% paraformaldehyde), permeabilized (0.1% TX-100) and pre-labeled with primary and secondary antibodies. The pre-labeling steps can be followed by dehydration, infiltration and embedment. Embedment, can be performed in EMbed-812. Thin (70 nm) sections can be cut on a Leica Ultracut3 microtome, collected on copper grids, and stained with Uranyl Acetate and Lead Citrate. Imaging can be performed on a Hitachi H7500 transmission electron microscope (TEM).

The methods described in this example can be used to define appropriate culture conditions that promote the differentiation of papillary epithelial cells into tubular epithelia. Fully polarized epithelia are expected to have intact and fully formed functional junctions (tight junctions, adherens junctions and desmosomes), express cytokeratin in lieu of vimentin and have distinct apical and basolateral plasma membrane protein compositions.

To exclude the possibility that any observed 'tubular epithelial differentiation' is not the result of contaminating epithelial cells in the papillary cell preparation, a homogenous population of CD133+, nestin+ cells, can be isolated as detailed above and maintained in culture for at least 6 passages. Primary tubular epithelial cells have a limited lifespan in culture and do not survive for more than six passages in culture. In the event that renal papillary cells fail to fully polarize, tight junctions may not be functional, N-cadherin may be expressed in lieu of E-cadherin, desmosomal components may be both apical and basolateral and cells may express fetal forms of cell surface proteins. If the cells only partially polarize and differentiate, irrespective of the in vitro culture conditions tried, it may be that an unknown differentiation factor is lacking or that the cells are incapable of replacing tubular epithelia. Studies using animal model systems, described below, may be employed to resolve this issue.

In Vitro Study of Renal Tubulogenesis in a 3D Collagen Gel Culture System

Cells grown in 3D collagen cell culture define their orientation in a relatively isotropic environment, migrate and interact with the extracellular matrix in three dimensions, are more resistant to apoptosis, and are capable of secreting extracellular matrix components and growth factors. Overall, three dimensional collagen gel cultures more closely resemble in vivo growth conditions than 2D culture [15]. MDCK cells grown in this system self-organize in hollow spheres, or cysts, formed by a monolayer of polarized epithelial cells. Treatment of these cysts with HGF causes them to form branching tubules [15]. As described herein, primary renal papillary cells can be cultured in 3D collagen 1 gels for 10 days. When cultured alone, the cells remained immature, but when cocultured with normal cortical tubular epithelia, they became integrated into hollow spheres with budding tubules. Therefore, the methods described below can be used to identify conditions that may promote differentiation of renal papillary cells in 3D culture, as well as to determine if the cells cocultured with renal epithelia can differentiate and participate in tubulogenesis in vitro.

CD133+ renal papillary cells can be trypsinized, mixed with type I collagen and plated in culture dishes. The cultures can be grown in a renal epithelial cell growth media (Clonetics) supplemented with various growth factors as described above for 2D culture (HGF, LIF, TGFoeta2, EGF or FGF2). Expression of cell adhesion components (tight junctions, adherens junctions, desmosomes), mesenchymal markers (N-cadherin) and different lectins as markers for distal and proximal tubules can be used to analyze the differentiation state of the cells and confocal imaging and serial sectioning of isolated structures can be used to characterize the nature of the formed structures/tubules. Immunostaining of intact or 0.5 µm-thick serial cryo-sections can be performed according to known procedures (See FIGS. 18-23). If the sectioning of the collagen gel proves problematic, the whole culture from each well can be processed for immunostaining (FIGS. 18-21). Confocal images can be collected on a Zeiss Axiovert 100M inverted microscope, using a Zeiss LSM 5 10META system, which can image up to eight different channels. Optical sections can be collected with 0.5-1 mm steps and image reconstruction software can be used to generate a three-dimensional image of the structures.

In order to establish the optimal conditions for in vitro tubulogenesis, the efficacy of added inducing factors can be comparatively evaluated for their impact on the morphogenic potential of the CD133+ renal papillary cells. For coculture experiments, the papillary cells can be prelabeled with green fluorescent dye 5(6)-CFDA (Molecular probes).

Under 3D cell culture conditions, it is expected that putative adult renal stem cells will form spherical structures, which over time will transition into tubule-resembling structures. These structures will possibly be formed by polarized epithelial-like cells. The addition of "inducing" morphogenic factors may even induce branching of the spheres and formation of more complex tubular structures. In the event that morphogenesis is seen only upon coculture with tubular epithelia, it would imply that an inducing signal derived from tubular epithelial cells is required. Thus, these methods may be used to establish if the interaction between pluripotent stem cells and fully polarized kidney epithelial cell is critical for the successful incorporation of the stem cells within damaged renal tissue.

Alternate matrix components may also be tested for their ability to promote papillary cell differentiation and tubulogenesis in 3D culture. The matrix components to be tested can be chosen based on demonstrated promise in the 2D culture systems as detailed in the previous section. The immunofluorescence analysis of 3D collagen-grown structures may be technically difficult, though we have obtained quite reasonable results in our preliminary studies. Recently published methods may be used to improve image quality and reduce technical artifacts if necessary [46]. According to some embodiments, the collagen-grown samples are pre-treated with dilute collagenase (10 minutes at 37° C.), blocked with fish skin gelatin and subsequently incubated with primary antibodies for 12-24 hours at room temperature with azide. Alexa-conjugated secondary antibodies (Molecular probes, Eugene, Oreg.) may be used for staining. Incubation with secondary antibodies is also done for 12-24 hours.

Developing Gene Expression Profiles

At present there is paucity of information to allow the rapid and definitive identification of adult renal stem cells. Only very recently, has a microarray study of renal progenitors derived from murine embryonic day 10.5 uninduced metanephric mesenchyme been published [47]. The definitive characteristics of renal stem cells are largely unknown and for the most part limited, best guess markers are used for characterization. Many of the commonly used markers are cell surface proteins defined by monoclonal antibodies or derived from genetic analyses of kidney development [21,48]. Consequently, adult stem cell characterization requires lengthy and detailed analyses such as the methods described above. However, once characterization is complete and a bona fide adult renal stem cell population is identified, future studies would benefit from the availability of a definitive gene expression profile that could be used to identify, isolate, and monitor such cells. For example, it is expected that adult renal stem cells will express novel cell surface markers that may be used for their specific isolation and enrichment (as has been done for hematopoietic stem cells). In addition, tracing changes in the gene expression of entire subsets of genes would offer a rapid and sensitive method for monitoring differentiation potential as compared to the more labor intensive methods currently used for monitoring changes in differentiation specific protein markers.

Using the methods described herein, a renal papillary stem cell expression profile can be established that may be used for comparisons with other renal stem cells and facilitate isolation and characterization of these elusive cells. Once the long-term culture characteristics and differentiation potential of papillary stem cells have been established, RNA from different patient samples can be isolated under conditions promoting retention of stem cell properties. The RNA can be used to develop hybridization probes and perform Affjmetrix Genechip® analyses using the same HG-U133 chips described above. Data analysis can be performed using suitable software such as Affymetrix Microarray Suite v5.0 software and Genespring (Silicon Genetics). The gene expression data can be normalized to the average of all the samples. Comparisons with the average profiles of normal kidney epithelial cell samples can be used to identify stem cell specific genes and determine changes in fold expression upon differentiation. Based on comparative studies between ADPKD and normal kidney cells it is not unreasonable to believe that the methods described herein may be employed to identify as many as 100 or more differentially regulated genes. The use of 3-6 independent patient samples has been found to minimize irrelevant patient-to-patient variability. To validate genes identified through this screening and delineate those most actively changing during early differentiation, a given number, such as ten, candidate genes exhibiting the largest differences in expression between stem cells and fully differentiated epithelia may be selected and kinetic studies performed using established protocols for real-time PCR (available in the KUGR facility).

Real time PCR studies can be performed using 2D cell cultures and conditions identified to induce renal papillary cell differentiation into tubular epithelia. The establishment of a renal stem cell gene expression profile is important to speed cell analysis and facilitate purification.

The presently described methods may be used to identify a renal stem cell expression profile that encompasses some of the known factors regulating kidney development such as Pax2, WTI [21,47]. These methods may further be used to identify new factors that may be important for adult stem cell survival. For example, increases in E-cadherin and the kidney specific cadherin16 may be found to accompany epithelial differentiation [23]. Thus, the present methods may be used to gain insight into the temporal sequence of events necessary for epithelial differentiation from adult stem cells. Furthermore, the present methods may be used to define a unique gene expression profile that can be used for defining novel cell surface markers for routine adult renal stem cell isolation and characterization. Such information can then be used to assay the distribution of adult renal stem cells in the whole kidney.

Contribution of Papillary Cells to Tubular Regeneration

Animal models and metanephric organ culture are commonly used to test the capacity of stem cells to differentiate in vivo. Animal studies can be used to define the optimal system for testing human stem cells in an in vivo animal model system. Two live animal models have been used to study implanted renal stem cells. A rat model readily allows for direct implantation of cells under the kidney cortex with or without renal ischemic injury. The problem with the rat model system is the possibility of immune rejection when used for xenotransplantation, though cyclosporine has been used effectively to alleviate this problem. SCID mice, lacking T- and B-lymphocyte development, have been used extensively for human hematopoietic stem cell transplantation studies. Recent studies report on the xenotransplantation of human CD133+ kidney cells (derived by immunoisolation from kidney cortex) via infusion into the SCID mouse model [32]. However, renal homing could only be observed following glycerol induced, renal ischemic injury. According to some embodiments, a rat model may be preferable because the cells can be more directly implanted and followed with or without renal injury. Furthermore, there are well-developed methods for assessing effects on kidney function in the rat model.

Inbred Wistar albino male rats weighing between 250-300 gm, aged three-six months can be used to minimize variation between animals (Harlan, Indianapolis, Ind.). Rats can be xenotransplanted with a putative human papillary derived stem cells. The migration of human papillary cells and resulting parenchymal or tubular incorporation can be assessed for cells derived from three different human patients, and a subset of the animals can undergo surgery without xenotransplantation as controls. Cyclosporjn A (Sandimmune; Novartis Pharma LTD, Basel Switzerland) is routinely used as an immunosuppressant. Rats can be given 30 mg/kg Cyclosporin Alday, a dose commonly used to inhibit xenotransplant rejection. Transplanted rats can be given free access to water and pelleted food.

Xenotransplantation of Human Cells Beneath Rat Kidney Capsule

Fasted (24 hour) male, Wistar albino rats can be anesthetized and the left kidney palpated and exteriorized. Human kidney cells can be injected beneath the renal capsule ($1 \times 10^6$ human papillary, CD133, nestin positive cells prelabeled with BrdU and green fluorescent dye 5(6)-CFDA (Molecular probes) and suspended in Hanks buffered saline solution containing 0.02% EDTA to prevent aggregation) as done for rodent papillary cells [1]. The kidney can be reinternalized and the animals sutured to close the wound. After 7-14 days the animals can be sacrificed, the kidneys per-fused and fixed with 4% paraformaldehyde, the engrafted kidney can be removed and processed for light and electron microscopy. The contralateral kidney can serve as the control. The kidneys can be bisected and one half can be fixed in 10% neutral buffered formalin and processed for hematoxylin and eosin staining to examine kidney histology according to standard procedures. The other half can be dissected into 1×1 mm cubes, fixed and cryopreserved according to standard procedures [35]. Hematoxylin eosin stained sections can be examined for tubular cell swelling, cellular vacuolization, pyknotic nuclei and moderate to severe necrosis to evaluate for signs of renal injury. Cryosections can be prepared as previously described [35] and immunostained with antibodies against human HLA I or BrdU and appropriately conjugated secondary antibodies. Human papillary cells can be identified by the expression of human HLA I, and the presence of BrdU and/or 5(6)-CF3A green staining. Tubular epithelia can be classified using lectin staining; *Tetragonobulus purpureas* lectin for proximal and *Dolichos biflorus* or peanut lectin for distal tubules as documented in our published work [34, 35]. The samples can be imaged on a Zeiss META laser scanning microscope, capable of discriminating up to eight different fluorophores. The integration of the human cells can be further assessed by immunoelectron microscopy using our published procedures [44,45].

Induction of Transient Renal Ischemia

A pilot study can be performed with two rats at the outset (one non-ischemic control) to test whether or not transient renal ischemic injury alters the capacity of the human xenotransplanted cells to become incorporated into renal tubules. Fasted, 250-300 gm male, Wistar albino rats can be anesthetized and the left kidney exposed as detailed in the previous section. Ischemia can be induced by placing a small vascular clamp on the left renal pedicle for 45 minutes [49]. During the time of renal ischemia the animal can be maintained at 37° C. using a heating blanket. After 7 days the animals can be sacrificed and the distribution and differentiation status of the xenotransplanted human kidney cells can be assessed.

Kidney Function Assessment

Tail bleeds can be performed one week before surgery and immediately before sacrifice. Typically tail bleeds are performed after 24 hours of fasting. The blood samples can be collected into anticoagulant EDTA solution and the cells removed by centrifugation. The plasma can be used for enzymatic determinations of BUN (22 mg/di), creatinine (0.8-0.9 mg/dl) and urea levels. Urine samples can also be collected to measure urea (0.22 ml/rnin) and creatinine (0.5 ml/min) clearance. In the event of renal ischemic injury induced by the procedures, the normal values for serum creatinine and BUN are expected to increase by 4-5 fold, similarly the urinary clearance of urea and creatinine would decrease 4-5 fold from the normal values [50].

Data from experimental replicates can be used to calculate SEM with respect to kidney function and can be compared to the values obtained from sham operated controls. If the number of replicates is adequate, one way analysis of variance (ANOVA) and Student-Newman-Keuls test can be applied to evaluate if there is any statistically significant change between the experimental and control groups in terms of kidney function as a result of the xenotransplantation. $P<0.05$ considered can be considered statistically significant.

Based on published autologous transplantation studies of rat renal papillary cells, the xenotransplanted cells can be incorporated into kidney tubules and possibly the parenchyma. Quantitative assessment of the capacity of the transplanted cells to incorporate into different nephron segments, and assessment of the statistical distribution between parenchyma and tubules can then be performed.

Immunoelectron microscopy can establish if the human cells (identified as HLA I and BrdU positive) exhibit a differentiated phenotype corresponding to the tubule in which it is resident. In the event that xenotransplanted cells fail to incorporate into rat renal tubules and exhibit differentiated cell characteristics, the SCID mouse model can be used.

Another alternative to live animal studies may be to inject the human cells into metanephric organ cultures derived from embryonic mice [51].

Stem cells may provide a powerful new method to treat numerous pathophysiological disorders. The proper differentiation of stem cells within damaged tissue or organ is necessary to guarantee the participation of these cells in the regeneration process. According to one embodiment of the present invention, the differentiation of a putative pluripotent adult kidney stem cell population derived from renal papilla can be studied in cell culture. The studies can confirm their identity as active renal progenitor cells and test their ability to differentiate into tubular epithelia. The conditions necessary to induce the expression of the full complement of programs specifying a mature tubular epithelial cell can be determined using in vitro and in vivo model systems. Conditions promoting morphogenesis and differentiation of renal adult stem cells can provide insights into the possible utility of these cells in renal tubular epithelial tissue regeneration. Genechip® assays can define a gene expression profile for adult human renal stem cells, thereby aiding identification and further characterization of these elusive and understudied cells.

In example 1, cells were isolated from the papilla at the same time normal tubular epithelial cells were routinely harvested from the renal cortex. It will be appreciated that additional normal kidneys can be procured as a source for the routine isolation of papillary cells from normal adult kidney. Five to six papilla may be isolated from one kidney, yielding ~5×10$^6$ cells. These may be expanded through multiple passages.

Example 3

Co-Culture of Isolated Papillary Renal Stem Cells

One of the main identifying features of stem cells is their ability to adopt different cell fates or to propogate in an undifferentiated stem cell form. We observed that some of our isolated papillary renal stem cells formed cluster-like structures when placed in media lacking serum and containing 20 ng/ml EGF. The structures resembled those formed by neuronal stem cells called neurospheres. Neurosphere formation is considered a hallmark of undifferentiated neural stem cells.

Papillary renal stem cells were co-cultured with either differentiated adult human kidney tubule cells or embryonic neural stem cells to evaluate effects of cell secreted factors on renal stem cell plasticity and ability to grow in an undifferentiated state. In this co-culture system, renal stem cells were plated on porous cell culture inserts and co-cultured with neural stem cells, isolated from E-14 mouse embryo. The cells were cultured in defined serum-free DMEM/F12 medium containing 15 mM HEPES and 2.5 mM L-glutamine, with addition of 3 mM sodium bicarbonate, 25 µg/ml insulin, 16 µg/ml putrescin, 30 nM sodium selenite, 100 µg/ml apotransferrin and 20 µM progesterone. Following 3-4 days of culture, renal stem cells dramatically changed their shape and formed clusters of cells, morphologically resembling neurospheres. The spheres were positive to stem cell markers CD133 and nestin. Renal cortical tubular epithelial cells grown under the same conditions did not exhibit a change in their phenotype and did not form sphere-like structures. The results show that isolated renal stem cells exhibit features of typical stem cells: they express stem cell markers, they are able to form neurosphere-like structures and exhibit strong morphological plasticity.

Sources of Material

Human Kidney Tissue

Donor kidneys from males and females ages 40-70 could be suitable for use for the methods described herein. Kidneys could be considered normal if no history of kidney disease, no renal carcinoma evident and no ischemic injury. Kidneys may be obtained from deceased organ donors whose kidneys are deemed unsuited for transplantation for clinical reasons. The kidneys could be used to isolate papillary stem cell populations.

Animal Model

Inbred Wistar albino male rats weighing between 2.50-300 gm, aged three-six months can be used (Harlan, Indianapolis, Ind.). Rats can be xenotransplanted with a putative human papillary derived stem cells from each human patient. The migration of human papillary cells and resulting parenchymal or tubular incorporation can be assessed for cells derived from, for example, three different human patients, and, for example, three animals can undergo surgery without xenotransplantation (requiring nine rats in total). Cyclosporin A (Sandimrnune; Novartis Pharma LTD, Basel Switzerland) is routinely used as an immunosuppressant. Rats can be given 30 mg/kg Cyclosporin Alday, a dose commonly used to inhibit xenotransplant rejection.

Xenotransplantation of Human Cells Beneath Rat Kidney Capsule

Fasted (24 hours) male, Wistar albino rats can be anesthetized with isoflurane gas (administration of inhaled anesthetics is preferred over injected anesthetic due to the improved recovery and reduced mortality). The rats can be placed on their right side and the left side shaved and cleaned with ethanol. The left kidney can be palpated and exteriorized through a 1-5-cm subcostal incision at the costo-vertebral angle. The externalized kidney can be secured and a small incision made with a scalpel in the renal capsule at the anterior pole of the kidney. The renal capsule can be gently lifted with fine curved forces and a blunt curved glass micmspatula can be used to separate the capsule from the surface of the kidney to create a space for the xenografted cells. Human kidney cells (1×10$^6$ human papillary, CD133, nestin positive cells prelabeled with BrdU and green fluorescent dye 5(6)-CFDA (Molecular. probes) and suspended in Hanks buffered saline solution containing 0.02% EDTA to prevent aggregation) can be injected beneath the renal capsule. Three injections of 20 µl each of cells and medium is well-tolerated [1]. The kidney can be reinternalized and the muscle layer and skin closed using 4-0 chromic catgut and a stapler, respectively. After 7-14 days the animals can be sacrificed, the kidneys perfused and fixed with 4% paraformaldehyde, and the engrafted kidney removed and processed for light and electron microscopy. The contralateral kidney can serve as a control. The kidneys can be bisected and one half can be fixed in 10% neutral buffered formalin and processed for hematoxylin and eosin staining to examine kidney histology according to standard procedures. The other half can be dissected into 1×1 mm cubes, fixed and cryopreserved according to standard procedures [35]. Hematoxylin eosin stained sections can be examined for tubular cell swelling, cellular vacuolization, pyknotic nuclei and moderate to severe necrosis to evaluate for signs of renal injury. A minimum of 10 fields for each kidney slide can be examined and assigned a severity score on a scale of none (−), mild (+), moderate (++) and severe (+++) damage. Cryosections can be prepared as previously described in Silberberg, 2005 and immunostained with antibodies against human HLA I or BrdU and an appropriately conjugated secondary antibody. Human papillary cells can be identified by the expression of human HLA I, and the presence of BrdU and/or 5(6)-CFDA green staining. Tubular epithelia can be classified using lectin staining; Tetragonobulus purpureas lectin for proximal and Dolichos biflorus or peanut lectin for distal tubules as documented in our published work [Roitbak, 2004; Silberberg, 2005]. The samples can be imaged on a Zeiss META laser scanning microscope, capable of discriminating up to eight different fluorophores. The integration of the human cells can be further assessed by immunoelectron microscopy using published procedures [49].

Induction of Transient Renal Ischemia

A pilot study can be performed with two rats at the outset (one non-ischemic control) to test whether or not transient renal ischemic injury alters the capacity of the human xenotransplanted cells to become incorporated into renal tubules. Fasted, 250-300 gm male, Wistar albino rats can be anesthetized and the left kidney exposed as detailed in the previous section. Ischemia can be induced by placing a small vascular clamp on the left renal pedicle for 4.5 minutes (Molitoris, J. Clin. Invest. 1985). During the time of renal ischemia the animal can be maintained at 37° C. using a heating blanket. After 7 days the animals can be sacrificed and the distribution and differentiation status of the xenotransplanted human kidney cells can be assessed.

Kidney Function Assessment

Tail bleeds can be performed one week before surgery and immediately before sacrifice. Typically, tail bloods are performed 24 hours after fasting. The blood samples can be collected into anticoagulant EDTA solution and the cells removed by centrifugation. The plasma can be used for enzymatic determinations of BUN (22.mg/dl), creatinine (0.8-0.9 mg/dl) and urea levels. Urine samples can also be collected to measure urea (0.22 ml/min) and creatinine (0.5 ml/min) clearance. In the event of renal ischemic injury induced by the procedures, the normal values for serum creatinine and BUN are expected to increase by 4-5 fold. Similarly the urinary clearance of urea and creatinine would decrease 4-5 fold from the normal values. Data from experimental replicates can be used to calculate SEM with respect to kidney function and can be compared to the values obtained from the three Sham operated controls. One way analysis of variance (ANOVA) and Student-Newman-Keuls test can be applied to evaluate if there is any statistically significant change between the experimental and control groups in terms of kidney function as a result of the xenotransplanation. $P<0.05$ considered could be considered statistically significant.

LIST OF REFERENCES CITED

1. Oliver, J. A., O. Maarouf, F. H. Cheema, T. P. Martens, and Q. Al-Awqati The Renal Papilla Is a Niche for Adult Kidney Stem Cells. J Clin Invest, 2004. 114:795-804.
2. Atala, A. Tissue Engineering for the Replacement of Organ Function in the Genitourinary System. Am J Transplant, 2004. 4 Suppl 6:58-73.
3. Anglani, F., M. Forino, D. Del Prete, E. Tosetto, R. Torregrossa, and A. D'Angelo In Search of Adult Renal Stem Cells. J Cell Mol Med. 2004. 8:474-487.
4. Ricardo, S. and J. Deane Adult Stem Cells in Renal Injury and Repair. Nephrology, 2005. doi:10.1111/j.1440-1797.2005.00373.x.
5. Slack, J. M. Stem Cells in Epithelial Tissues. Science, 2000. 287:1431-1433.
6. Kubo, A., K. Shinozaki, J. M. Shannon, V. Kouskoff, M. Kennedy, S. Woo, H. J. Fehling, and G. Keller Development of Definitive Endoderm from Embryonic Stem Cells in Culture. Development, 2004. 131:1651-1662.
7. Teramoto, K., Y. Hara, Y. Kumashiro, R. Chinzei, Y. Tanaka, K. Shimizu-Saito, K. Asahina, H. Teraoka, and S. Arii Teratoma Formation and Hepatocyte Differentiation in Mouse Liver Transplanted with Mouse Embryonic Stem Cell-Derived Embroid Bodies. Transplant Proc, 2005. 37:285-286.
8. Nardi, N. B. All the Adult Stem Cells, Where Do They All Come From? An External Source for Organ-Specific Stem Cell Pools. Med Hypotheses, 2005. 64:811-817.
9. Leedham, S. J., M. Brittan, S. A. McDonald, and N. A. Wright Intestinal Stem Cells. J Cell Mol Med, 2005. 9:11-24.
10. Abbattista, M. R. and F. P. Schena Stem Cells and Kidney Diseases. Minerva Med, 2004. 95:411-418.
11. Maeshima, A., S. Yamashita, and Y. Nojima Identification of Renal Progenitor-Like Tubular Cells That Participate in the Regeneration Processes of the Kidney. J Am Soc Nephrol, 2003. 14:3138-3146.
12. Sherley, J. L. Asymmetric Cell Kinetics Genes: The Key to Expansion of Adult Stem Cells in Culture. Scientific World Journal, 2002. 2:1906-1921.
13. Potten, C. S., G. Owen, and D. Booth Intestinal Stem Cells Protect Their Genome by Selective Segregation of Template DNA Strands. J Cell Sci, 2002. 115:2381-2388.
14. Rambhatla, L., S. Ram-Mohan, J. J. Cheng, and J. L. Sherley Immortal DNA Strand Cosegregation Requires P53/Impdh-Dependent Asymmetric Self-Renewal Associated with Adult Stem Cells. Cancer. Res, 2005. 65:3155-3161.
15. Zegers, M. M., L. E. O'Brien, W. Yu, A. Datta, and K. E. Mostov Epithelial Polarity and Tubulogenesis in Vitro. Trends Cell Biol, 2003. 13:169-176.
16. Yoshino, K., J. S. Rubin, K. G. Higinbotham, A. Uren, V. Anest, S. Y. Plisov, and A. O. Perantoni Secreted Frizzled-Related Proteins Can Regulate Metanephric Development. Mech Dev, 2001. 102:45-55.
17. Barasch, J., J. Yang, C. B. Ware, T. Taga, K. Yoshida, H. Erdjument-Bromage, P. Tempst, E. Parravicini, S. Malach, T. Aranoff; and J. A. Oliver Mesenchymal to Epithelial Conversion in Rat Metanephros Is Induced by Lif: Cell, 1999. 99:377-386.
18. Plisov, S. Y., K. Yoshino, L. F. Dove, K. G. Higinbotham, J. S. Rubin, and A. O. Perantoni Tgf Beta 2, Lif and Fgf2 Cooperate to Induce Nephrogenesis. Development, 2001. 128:1045-1057.
19. Takito, J. and Q. Al-Awqati Conversion of Es Cells to Columnar Epithelia by Hensin and to Squamous Epithelia by Laminin. J Cell Biol, 2004. 166:1093-1102.
20. Dressler, G. Tubulogenesis in the Developing Mammalian Kidney. Trends Cell Biol, 2002. 12:390-395.
21. Bouchard, M. Transcriptional Control of Kidney Development. Differentiation, 2004. 72:295-306.
22. Dahl, U., A. Sjodin, L, Larue, G. L. Radice, S. Cajander, M. Takeichi, R. Kemler, and H. Semb Genetic Dissection of Cadherin Function During Nephrogenesis. Mol Cell Biol, 2002. 23. 22:1474-1487.
24. Hishikawa, K., T. Marumo, S. Miura, A. Nakanishi, Y. Matsuzaki, K. Shibata, H. Kohike, T. Komori, M. Hayashi, 24. T. Nakaki, H. Nakauchi, H. Okano, and T. Fujita Leukemia Inhibitory Factor Induces Multi-Lineage Differentiation of Adult Stem-Like Cells in Kidney Via Kidney-Specific Cadherin 16. Biochem Biophys Res Commun, 2005. 328: 288-291.
25. Gumbiner, B. M. Cell Adhesion: The Molecular Basis of Tissue Architecture and Morphogenesis. Cell, 1996. 84:345-357.
26. Angst, B. D., C. Marcozzi, and A. I. Magee The Cadherin Superfamily: Diversity in Form and Function. J Cell Sci, 2001. 114:629-641
27. Yap, A. S., W. M. Brieher, and B. M. Gumbiner Molecular and Functional Analysis of Cadherin-Based Adherens Junctions. Annu Rev Cell Dev Biol, 1997. 13:119-146.
28. Gottardi, C. J, E. Wong, and B. M. Gumbiner E-Cadherin Suppresses Cellular Transformation by Inhibiting Beta-Catenin Signaling in an Adhesion-Independent Manner. J Cell Biol, 2001. 153:1049-1060.
29. Horster, M. F., G. S. Braun, and S. M. Huber Embryonic Renal Epithelia: Induction, Nephrogenesis, and Cell Differentiation. Physiol Rev, 1999. 79:1157-1191.
30. Jiang, Y., B. N. Jahagirdar, R. L. Reinhardt, R. E. Schwartz, C. D. Keene, X. R. Ortiz-Gonzalez, M. Reyes, T. Lenvik, T. Lund, M. Blackstad, J. Du, S. Aldrich, A. Lisberg, W. C. Low, D. A. Largaespada, and C. M. Verfaillie Pluripotency of Mesenchymal Stem Cells Derived from Adult Marrow. Nature, 2002. 418:41-49.
31. Herrera, M. B., B. Bussolati, S. Bruno, V. Fonsato, G. M. Romanazzi, and G. Camussi Mesenchymal Stem Cells Contribute to the Renal Repair of Acute Tubular Epithelial Injury, Int J Mol Med, 2004. 14:1035-1041.
32. Stokman, G., J. C. Leemans, N. Claessen, J. J. Weening, and S. Florquin Hematopoietic Stem Cell Mobilization Therapy Accelerates Recovery of Renal Function Independent of Stem Cell Contribution. J Am Soc Nephrol, 2005. 16:1684-1692.
33. Bussolati, B., S. Bruno, C. Grange, S. Buttiglieri, M. C. Deregibus, D. Cantino, and G. Camussi Isolation of Renal Progenitor Cells from Adult Human Kidney. Am J Pathol, 2005. 166:545-555.
34. Charson, A. J., S. Nakamura, R. Bacallao, and A. Wandinger-Ness Compromised Cytoarchitecture and Polarized Trafficking in Autosomal Dominant Polycystic Kidney Disease Cells. J Cell Biol, 2000. 149:111-124.
35. Roitbak, T., C. J. Ward, P. C. Harris, R. Bacallao, S. A. Ness, and A. Wandinger-Ness A Polycystin-1 Multiprotein Complex Is Disrupted in Polycystic Kidney Disease Cells. Mol Biol Cell, 2004. 15:1334-1346.
36. Silberberg, M., A. J. Charron, R. Bacallao, and A. Wandinger-Ness Mispolarization of Desmosomal Proteins and Altered Intercellular Adhesion in Autosomal Dominant Polycystic Kidney Disease. Am J Physiol Renal Physiol, 2005, 288:F1153-1163.
37. Roitbak, T., Z. Surviladze, R. Tikkanen, and A. Wandinger-Ness A Polycystin Multiprotein Complex Constitutes a Cholesterol-Containing Signaling Microdomain in Human Kidney Epithelia. Biochem. J., 2005. Under revision.
38. van Adelsberg, J., J. C. Edwards, I. Takito, B. Kiss, and Q. al-Awqati An Induced Extracellular Matrix Protein Reverses the Polarity of Band 3 in Intercalated Epithelial Cells. Cell, 1994. 76:1053-1061.
39. Weigmann, A., D. Corbeil, A. Hellwig, and W. B. Huttner Prominin, a Novel Microvilli-Specific Polytopic Membrane Protein of the Apical Surface of Epithelial Cells, Is Targeted to Plasmalemmal Protrusions of Non-Epithelial Cells. Proc Natl Acad Sci USA, 1997. 94:12425-12430.
40. Fargeas, C. A., D. Corbeil, and W. B. Huttner Ac133 Antigen, Cd133, Prominin-1, Prominin-2, Etc.: Prominin Family Gene Products in Need of a Rational Nomenclature. Stem Cells, 2003. 21:506-508.
41. Carone, F. A., S. Nakamura, B. S. Schumacher, P. Punyarit, and K. D. Bauer Cyst-Derived Cells Do Not Exhibit Accelerated Growth or Features of Transformed Cells in Vitro. Kidney Int, 1989. 35:1351-1357.
42. Charron, A. J., R. L. Bacallao, and A. Wandinger-Ness Adpkd: A Human Disease Altering Golgi Function and Basolateral Exocytosis in Renal Epithelia. Traffic, 2000. 1:675-686.
43. Danet, G. H., Y. Pan, J. L,. Luongo, D. A. Bonnet, and M. C. Simon Expansion of Human Scid-Repopulating Cells under Hypoxic Conditions. J Clin Invest, 2003. 112:126-135.
44. Morrison, S. J., M. Csete, A. K. Groves, W. Melega, B. Wold, and D. J. Anderson Culture in Reduced Levels of Oxygen Promotes Clonogenic Sympathoadrenal Differentiation by Isolated Neural Crest Stem Cells. J Neurosci, 2000. 20:7370-7376.
45. Stein, M. P., Y. Feng, K. L. Cooper, A. M. Welford, and A. Wandinger-Ness Human Vps34 and PI50 Are Rab7 Interacting Partners. Traffic, 2003. 4:754-771.
46. Dong, J., W. Chen, A. Welford, and A,. Wandinger-Ness The Proteasome Alpha-Subunit Xapc7 Interacts Specifically with Rab7 and Late Endosomes. J Biol Chem, 2004. 279:21334-21342.
47. Pollack, A. L., R. B. Runyan, and K. E,. Mostov Morphogenetic Mechanisms of Epithelial Tubulogenesis: Mdck Cell Polarity Is Transiently Rearranged without Loss of Cell-Cell Contact During Scatter Factor Mepatocyte Growth Factor-Induced Tubulogenesis. Dev Biol, 1998. 204:64-79.
48. Challen, G. A., G. Martinez, M. J. Davis, D. F. Taylor, M. Crowe, R. D. Teasdale, S. M. Grirnrnond, and M. H. Little Identifying the Molecular Phenotype of Renal Progenitor Cells. J Am Soc Nephrol, 2004. 15:2344-2357.
49. Mason et al., CD Antigens 2002. Blood, 2002. 99:3877-3880.
50. Molitoris et al., Ischemia Induces Partial Loss of surface Membrane Polarity and Accumulation of Putative Calcium Ionophores. J Clin Invest, 1985. 76:2097-2105.
51. Singh et al., Cyclosporine Protects against Ischemia/Reperfusion Injury in Rat Kidneys. Toxicology, 2005. 207: 339-347
52. Steenhard, B. M., K. S. Isom, P. Cazcarr. 0, J. H. Dunmore, A. R. Godwin, P. L. St John, and D. R. Abrahamson Integration of Embryonic Stem Cells in Metanephric Kidney Organ Culture. J Am Soc Nephrol, 2005. 16:1623-1631.

The complete disclosure of all patents, patent applications, publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. Moreover, all headings are for the convenience of the reader and should not be used to limit the meaning of the text that follows the heading.

The invention claimed is:

1. Isolated human renal adult stem cells, where the human renal stem cells were isolated from only the papillary region of human kidney, wherein the renal adult stem cells are surface positive for CD133 and intracellular nestin.

2. The isolated human renal stem cells of claim 1 further comprising an exogenous polynucleotide.

3. The isolated human renal stem cells of claim 2 wherein the exogenous polynucleotide encodes a therapeutic agent.

4. The isolated human renal stem cells of claim 1 maintained in a heterologous culture with embryonic rodent kidney stem cells.

5. The isolated human renal stem cells of claim 1 wherein the in situ cells were localized only in the loops of Henle in the papillary region of human kidney.

6. The isolated human renal stem cells of claim 1 wherein the cells are capable of forming neurosphere-like structures.

7. The isolated human renal stem cells of claim 1 xenotranplanted beneath the rodent kidney capsule.

8. The isolated human renal stem cells of claim 5 wherein the rodent kidney capsule is from a rat or mouse.

* * * * *